United States Patent
Zhou et al.

(10) Patent No.: US 10,888,853 B2
(45) Date of Patent: *Jan. 12, 2021

(54) CINCHONIUM BETAINE CATALYSTS AND METHODS OF USING SAME

(71) Applicant: Brandeis University, Waltham, MA (US)

(72) Inventors: Xiao Zhou, Waltham, MA (US); Yongwei Wu, Waltham, MA (US); Li Deng, Waltham, MA (US)

(73) Assignee: Brandeis University, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/740,447

(22) Filed: Jan. 12, 2020

(65) Prior Publication Data

US 2020/0147593 A1 May 14, 2020

Related U.S. Application Data

(63) Continuation of application No. 16/093,899, filed as application No. PCT/US2017/027633 on Apr. 14, 2017, now Pat. No. 10,610,857.

(60) Provisional application No. 62/323,426, filed on Apr. 15, 2016.

(51) Int. Cl.
| | | |
|---|---|---|
| *C07D 453/04* | (2006.01) | |
| *B01J 31/02* | (2006.01) | |
| *C07C 249/02* | (2006.01) | |
| *C07B 57/00* | (2006.01) | |
| *C07C 209/62* | (2006.01) | |
| *C07F 7/18* | (2006.01) | |
| *C07D 453/00* | (2006.01) | |

(52) U.S. Cl.
CPC .......... *B01J 31/0271* (2013.01); *B01J 31/02* (2013.01); *B01J 31/0244* (2013.01); *C07B 57/00* (2013.01); *C07C 209/62* (2013.01); *C07C 249/02* (2013.01); *C07D 453/00* (2013.01); *C07D 453/04* (2013.01); *C07F 7/1804* (2013.01); *B01J 2231/52* (2013.01); *C07C 2601/14* (2017.05)

(58) Field of Classification Search
CPC ...... C07D 453/04; B01J 31/02; B01J 31/0239
See application file for complete search history.

(56) References Cited

U.S. PATENT DOCUMENTS

| | | | |
|---|---|---|---|
| 3,627,749 A * | 12/1971 | Ackermann | ............ C09B 62/04 534/636 |
| 5,521,320 A | 5/1996 | Lee et al. | |
| 10,610,857 B2 * | 4/2020 | Zhou | ............ B01J 31/0271 |
| 2005/0208438 A1 * | 9/2005 | Yamamoto | ......... G03C 1/49854 430/619 |
| 2014/0234543 A1 | 8/2014 | Ito et al. | |

OTHER PUBLICATIONS

International Search Report and Written Opinion for PCT/US2017/027633, dated Jun. 30, 2017, 6 pages.
Zhou et al., "Cinchonium Betaines as Efficient Catalysts for Asymmetric Proton Transfer Catalysts: The Development of a Practical Enantioselective Isomerization of Imines," Journal of the American Chemistry Society, 138, 12297-12302 (2016).
Wu et al., "Asymmetric Synthesis Trifluoromethylated Amines via Catalytic Enantioselective Isomerization of Imines," Journal of the American Chemistry Society, 134, 14334-14337 (2012).
Office Action for U.S. Appl. No. 16/093,899, United States Patent and Trademark Office (dated May 29, 2019).

\* cited by examiner

*Primary Examiner* — Emily A Bernhardt
(74) *Attorney, Agent, or Firm* — Danielson Legal LLC

(57) ABSTRACT

Provided herein are cinchonium betaine catalysts and methods of promoting asymmetric imine isomerization reactions using the same.

20 Claims, 2 Drawing Sheets

CINCHONIUM BETAINE CATALYSTS AND METHODS OF USING SAME

CROSS REFERENCE TO RELATED APPLICATIONS

This patent application is a continuation of U.S. patent application Ser. No. 16/093,899, filed on Apr. 14, 2017 and now issued as U.S. Pat. No. 10,610,857, which is the U.S. national stage of International (PCT) Appl No. PCT/US2017/027633, filed on Apr. 14, 2017, which itself claims priority to and the benefit of U.S. Prov. Appl. No. 62/323,426, filed on Apr. 15, 2016. The entire contents of each of these applications are incorporated herein by reference.

STATEMENT OF RIGHTS TO INVENTIONS MADE UNDER FEDERALLY SPONSORED RESEARCH

This invention was made with government support under R01 GM061591 grant No. NIH GM 61591 awarded by the National Institutes of Health. The government has certain rights in the invention.

BACKGROUND

Chiral organic catalysts containing both a hydrogen bond donor and an acceptor can facilitate biomimetic 1,3-proton transfer catalysis to promote highly enantioselective olefin and imine isomerizations. These enantioselective isomerizations provide new access to valuable chiral building blocks such as α,β-unsaturated butenolides, a-amino acids, α,β-unsaturated cyclohexenones and trifluoromethylated amines. Catalysts such as dihydroquinine (DHQ) and dihydroquinidine (DHQD) have been developed for imine isomerizations and other asymmetric reactions such as Sharpless dihydroxylation. DHQ based catalysts afford one enantiomer, and DHQD catalysts give access to the opposite enantiomer. However, the high catalyst loading (10 mol %) and long reaction time (48-72 hours) has limited the application of this reaction in organic synthesis. DHQD catalysts often resulted in low enantioselectivity such that the ˆ-enantiomer product is not readily accessed in this reaction. Scheme 1 summarizes the current state of the art in asymmetric isomerization of trifluoromethyl imines with acid-base bifunctional catalysts.

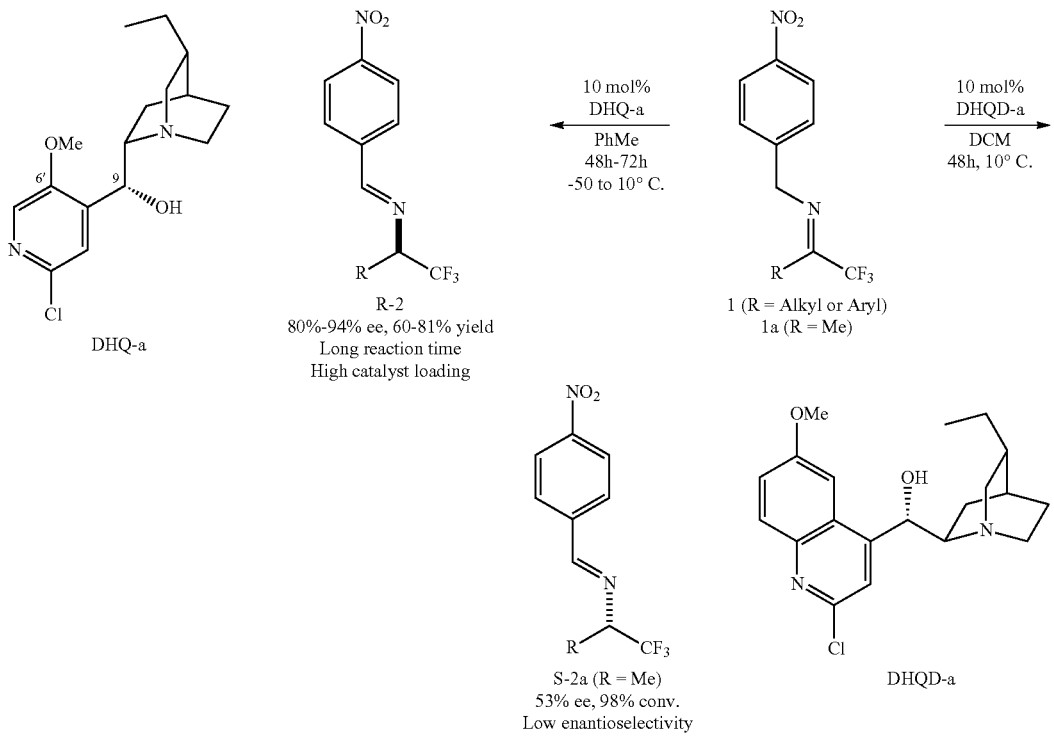

Thus, there is a need in the art to identify catalysts that can be used to promote imine isomerization reactions in high yield and enantiomeric excess. The presently disclosed compounds and methods meets this need.

SUMMARY

Provided herein are cinchonium betaine catalysts that can be used to promote imine isomerization in a highly chemoselective and enantioselective manner. In certain embodiments, the catalysts described herein allow for the asymmetric preparation of chiral amines.

Provided herein is a compound, or a salt, tautomer, enantiomer or diastereoisomer thereof, of formula (I):

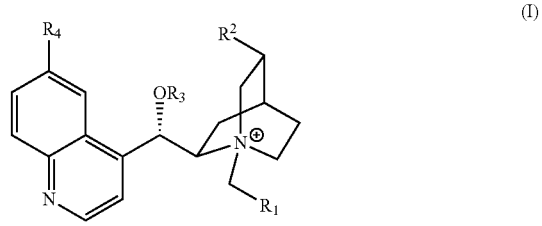

wherein:

R¹ is

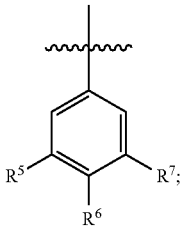

R⁵ and R⁷ are independently aryl;

R⁶ is alkoxy or alkylsiloxy;

R² is alkenyl;

R³ is optionally substituted heteroaryl, where each optional substituent is independently selected from aryl and halo; and R⁴ is —OH or —O⁻.

In some embodiments, R₅ and R₇ are each phenyl. In some embodiments, R₆ is selected from methoxy, t-butoxy and t-butyldimethylsiloxy. In some embodiments, R₂ is —CH=CH₂. In some embodiments, R₃ is R₃ is pyrimidinyl substituted with one or more groups selected from aryl and halo. For example, R₃ can be 4-chloro-2,5-diphenylpyrimidinyl (PYR). In some embodiments, R₄ is —OH while in other embodiments, R₄ is —O⁻.

In certain embodiments, the compound is at least one selected from:

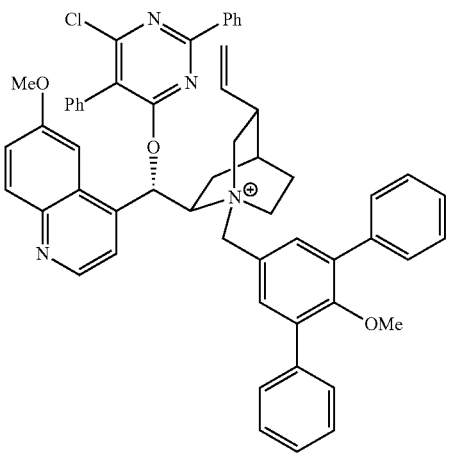 [SMILES: C=CC1C[N+]2(Cc3cc(-c4ccccc4)c(OC)c(-c4ccccc4)c3)CCC1CC2[C@@H](Oc1nc(-c2ccccc2)nc(Cl)c1-c1ccccc1)c1ccnc2ccc(OC)cc12]

(1,S',2R,4,S',5R)-2-(((,S)-((6-chloro-2,5-diphenylpyrimidin-4-yl)oxy)(6-methoxyquinolin-4-yl)methyl)-1-((2'-methoxy-[1,1':3',1''-terphenyl]-5'-yl)methyl)-5-vinylquinuclidin-1-ium (QD-8)

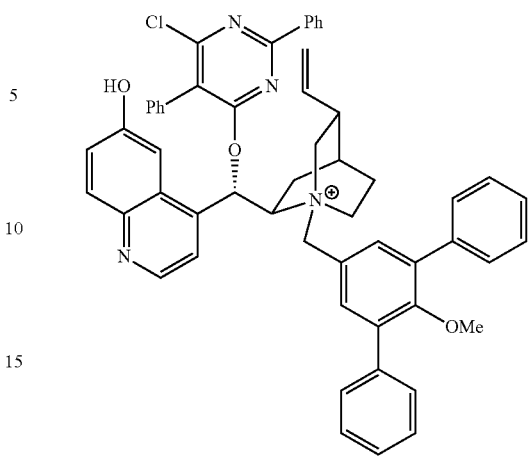

(1,S',2R,4,S',5R)-2-(((,S)-((6-chloro-2,5-diphenylpyrimidin-4-yl)oxy)(6-hydroxyquinolin-4-yl)methyl)-1-((2'-methoxy-[1, 1':3', 1''-terphenyl]-5'-yl)methyl)-5-vinylquinuclidin-1-ium (PQD-9)

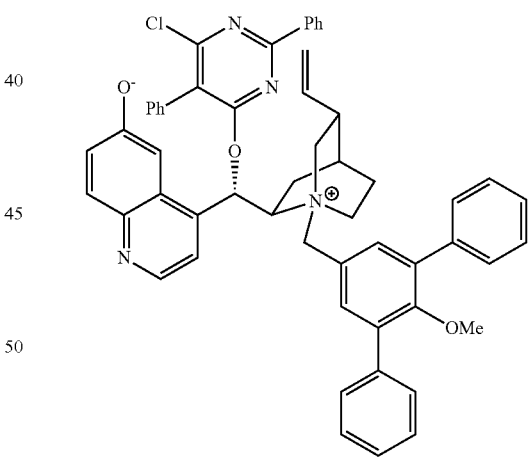

4-((5)-((6-chloro-2,5-diphenylpyrimidin-4-yl)oxy)((1^2R, 4^5R)-1-((2'-methoxy-[1,1':3',1''-terphenyl]-5'-yl)methyl)-5-vinylquinuclidin-1-ium-2-yl)methyl)quinolin-6-olate (QD-9a)

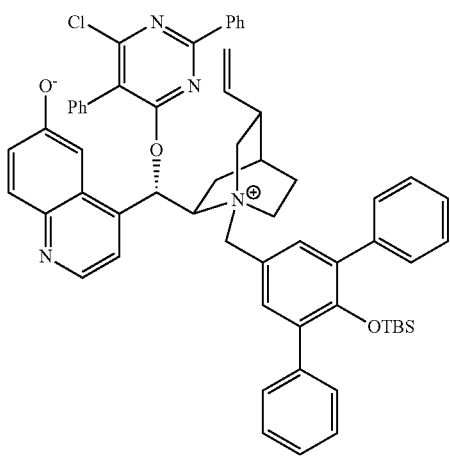 [SMILES: C=CC1C[N+]2(Cc3cc(-c4ccccc4)c(O[Si](C)(C)C(C)(C)C)c(-c4ccccc4)c3)CCC1CC2[C@@H](Oc1nc(-c2ccccc2)nc(Cl)c1-c1ccccc1)c1ccnc2ccc([O-])cc12]

4-((S)-((1S,2R,4^5R)-1-((2'-((tert-butyldimethylsilyl)oxy)-[1,1^3^r'^henyl]-5'-yl)methyl)-5-vinylquinuclidin-1-ium-2-yl)((6-chloro-2,5-diphenylpyrimidin-4-yl)oxy)methyl)quinolin-6-olate (QD-9b)

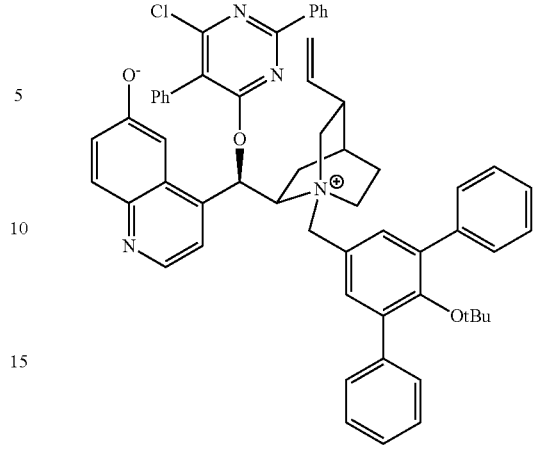

4-((R)-((1^2R,4^5R)-1-((2'-<tert-butoxy)-[1,1^3',r'-terphenyl]-5'-yl)methyl)-5-vinylquinuclidin-14um-2-yl)((6-chloro-2,5-diphenylpyrimidin-4-yl)oxy)methyl)quinolin-6-olate (Q-9c).

Provided herein is a method of promoting imine isomerization that comprises contacting the imine with at least one compound disclosed herein, wherein the imine comprises formula (II):

(II)

wherein:
$R^a$ is selected from optionally substituted alkyl, optionally substituted aryl, optionally substituted cycloalkyl, and optionally substituted alkenyl, where each optional substituent is independently selected from alkyl, alkoxy, and halo;
$R^b$ is trifluoromethyl; and
$R^c$ is aryl;
to afford a compound a compound of formula (III)

(III)

In some embodiments, $R^a$ is alkyl, such as methyl, ethyl and n-butyl. In other embodiments, $R^a$ is cycloalkyl, such as cyclohexyl. In some embodiments, $R^a$ is trans-styryl. In some embodiments, $R^a$ is phenyl, optionally substituted with methyl, methoxy or fluoro. In some embodiments, $R^c$ is phenyl substituted with a nitro group.

In certain embodiments, the imine and the at least one compound are contacted in a non-aqueous system in the presence of a base. In some embodiments, the base is a hydroxide, such as NaOH or KOH. In other embodiments, the base can be a carbonate base, such as $Na_2CO_3$ or $K_2CO_3$. The amount of base in the system can be catalytic, such as about 10 mol %.

4-((S)-((1S,2R,4S,5R)-1-((2'-(t^utoxy)-[1,1':3',1"-terphenyl]-5'-yl)methyl)-5-vinylquinuclidin-14um-2-yl)((6-chloro-2,5-diphenylpyrimidin-4-yl)oxy)methyl)quinolin-6-olate (QD-9c) and In some embodiments, the amount of the at least one compound in the system ranges from about 0.01 mol % to about 5 mol % with respect to the imine, such as about 0.01 mol % to about 0.1 mol %, such as about 0.05 mol % to about 1 mol %, such as about 0.1 mol % to about 0.5 mol %. In some embodiments, the amount of the at least one compound in the system is selected from about 0.01 mol %, about 0.02 mol %, about 0.05 mol %, about 0.08 mol %, about 0.1 mol %, about 0.2 mol %, about 0.3 mol %, about 0.4 mol %, and about 0.5 mol %.

BRIEF DESCRIPTION OF THE DRAWINGS

The following detailed description of exemplary embodiments can be better understood when read in conjunction with the appended drawings. It should be understood, however, that the disclosure is not limited to the precise arrangements and instrumentalities of the embodiments shown in the drawings.

FIG. 1A is a schematic illustration of an imine isomerization reaction. Without wishing to be bound by any theory, the synthetic scheme illustrates the 1,3-isomerization of imine 1a using catalyst C-7 in the presence of exogenous water/hydroxide. Two products can form, the undesired difluoroalkene 4a and the desired amine 2a.

DETAILED DESCRIPTION

Definitions

Figure 1A:
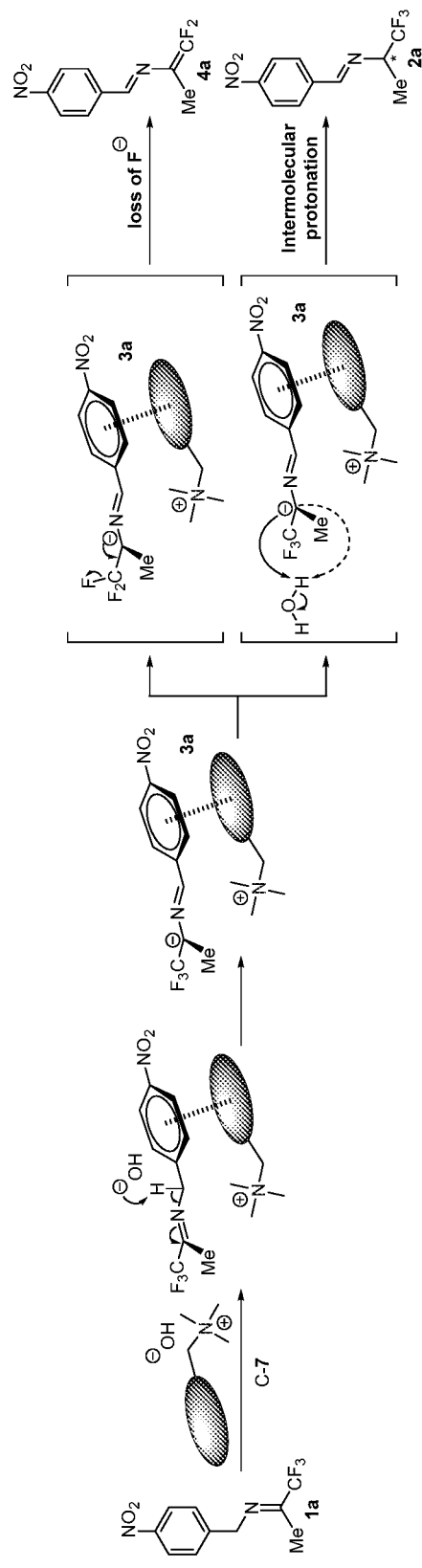

Unless defined otherwise, all technical and scientific terms used herein generally have the same meaning as commonly understood by one of ordinary skill in the art to which this disclosure pertains. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). Generally, the nomenclature used herein and the laboratory procedures in medicine, organic chemistry and polymer chemistry are those well known and commonly employed in the art.

As used herein, the articles "a" and "an" refer to one or to more than one (i.e., to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, such as ±5%, such as ±1%, and such as ±0.1% from the specified value, as such variations are appropriate to perform the disclosed methods.

As used herein, the term "alkyl", by itself or as part of another substituent means, unless otherwise stated, a branched or unbranched saturated hydrocarbon group. The term "n-alkyl" refers to an unbranched alkyl group. The term "$C_x$–$C_y$ alkyl" refers to an alkyl group having between x and y carbon atoms, inclusively, in the branched or unbranched hydrocarbon group. By way of illustration, but without limitation, the term "Ci-$C_8$ alkyl" refers to a straight chain or branched hydrocarbon moiety having from 1, 2, 3, 4, 5, 6, 7, or 8 carbon atoms. "Ci-$C_6$" refers to a straight chain or branched hydrocarbon moiety having from 1, 2, 3, 4, 5, or 6 carbon atoms. "$C_1$-$C_4$ alkyl" refers to a straight chain or branched hydrocarbon moiety having from 1, 2, 3, or 4 carbon atoms, including methyl, ethyl, n-propyl, iso-propyl, «-butyl, iso-butyl, sec-butyl, and ter t-butyl. The term "$C_1$-$C_4$ n-alkyl" refers to straight chain hydrocarbon moieties that have 1, 2, 3, or 4 carbon atoms including methyl, ethyl, n-propyl, and n-butyl.

As used herein, the term "alkenyl" by itself or as part of another substituent means, unless otherwise stated, a straight or branched hydrocarbon chain radical group consisting solely of carbon and hydrogen atoms, containing at least one double bond, and having from two to ten carbon atoms (i.e., $C_{2-10}$ alkenyl). Whenever it appears herein, a numerical range such as "2 to 10" refers to each integer in the given range; e.g., "2 to 10 carbon atoms" means that the alkenyl group can consist of 2 carbon atoms, 3 carbon atoms, etc., up to and including 10 carbon atoms. In certain embodiments, an alkenyl comprises two to eight carbon atoms. In other embodiments, an alkenyl comprises two to six carbon atoms (e.g., $C_{2-6}$ alkenyl). The alkenyl is attached to the parent molecular structure by a single bond, for example, ethenyl (i.e., vinyl), prop-1-enyl (i.e., allyl), but-1-enyl, pent-1-enyl, penta-1,4-dienyl, and the like. The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), 2-methylprop-2-enyl ($C_4$), butadienyl ($C_4$) and the like. Examples of $C_{2-6}$ alkenyl groups include the aforementioned $C_{2-4}$ alkenyl groups as well as pentenyl ($C_5$), pentadienyl ($C_5$), hexenyl ($C_6$), 2,3-dimethyl-2-butenyl ($C_6$) and the like, and the higher homologs and isomers. A non-limiting functional group representing an alkene is exemplified by —$CH_2$—CH=$CH_2$.

As used herein, the term "alkoxy" by itself or as part of another substituent means, unless otherwise stated, an —O-alkyl group, including from 1 to 10 carbon atoms of a straight, branched, saturated cyclic configuration and combinations thereof, attached to the parent molecular structure through an oxygen. Examples include methoxy, ethoxy, propoxy, isopropoxy, butoxy, t-butoxy, pentoxy, cyclopropyloxy, cyclohexyloxy and the like. In some embodiments, an alkoxy group can have one to six carbons denoted $C_1$-$C_3$. In some embodiments, $C_{1-4}$ alkoxy is an alkoxy group which encompasses both straight and branched chain alkyls of from 1 to 4 carbon atoms. In some aspects, the alkoxy group is a ($C_1$-$C_3$)alkoxy, such as, but not limited to, ethoxy and methoxy.

As used herein, the term "aryl" or "arene" employed alone or in combination with other terms means, unless otherwise stated, a radical with 6 to 14 ring atoms (e.g., $C_{6-14}$ aromatic or $C_{6-14}$ aryl) which has at least one ring having a conjugated pi electron system which is carbocyclic (e.g., phenyl, fluorenyl, and naphthyl). In some embodiments, the aryl is a $C_{6-io}$ aryl group. Whenever it appears herein, a numerical range such as "6 to 14 aryl" refers to each integer in the given range; e.g., "6 to 14 ring atoms" means that the aryl group can consist of 6 ring atoms, 7 ring atoms, etc., up to and including 14 ring atoms. The term includes monocyclic or fused-ring polycyclic (i.e., rings which share adjacent pairs of ring atoms) groups. In a multi-ring group, only one ring is required to be aromatic, so groups such as indanyl are encompassed by the aryl definition. Non-limiting examples of aryl groups include phenyl, phenalenyl, naphthalenyl, tetrahydronaphthyl, phenanthrenyl, anthracenyl, fluorenyl, indolyl, indanyl, and the like.

As used herein, the term "cycloalkyl" by itself or as part of another substituent means, unless otherwise stated, a monocyclic or polycyclic radical that contains only carbon and hydrogen, and can be saturated or partially unsaturated. Partially unsaturated cycloalkyl groups can be termed "cycloalkenyl" if the carbocycle contains at least one double bond, or "cycloalkynyl" if the carbocycle contains at least one triple bond. Cycloalkyl groups include groups having from 3 to 13 ring atoms (i.e., $C_3$-$C_{13}$ cycloalkyl). Whenever it appears herein, a numerical range such as "3 to 10" refers to each integer in the given range; e.g., "3 to 13 carbon atoms" means that the cycloalkyl group can consist of 3 carbon atoms, 4 carbon atoms, 5 carbon atoms, etc., up to and including 13 carbon atoms. The term "cycloalkyl" also includes bridged and spiro-fused cyclic structures containing no heteroatoms. The term also includes monocyclic or fused-ring polycyclic (i.e., rings which share adjacent pairs of ring atoms) groups. In some embodiments, it is a $C_3$-$C_8$ cycloalkyl radical. In some embodiments, it is a $C_3$-$C_6$ cycloalkyl radical. Illustrative examples of cycloalkyl groups include, but are not limited to the following moieties: $C_{3-6}$ carbocyclyl groups include, without limitation, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$) and the like. Examples of C3-7 carbocyclyl groups include norbornyl ($C_7$). Examples of $C_{3-8}$ carbocyclyl groups include the aforementioned $C_{3-7}$ carbocyclyl groups as well as cycloheptyl($C_7$), cycloheptadienyl ($C_7$), cycloheptatrienyl ($C_7$), cyclooctyl ($C_8$), bicyclo[2.2.1]heptanyl, bicyclo[2.2.2]octanyl, and the like. Examples of $C_{3-C13}$ carbocyclyl groups include the aforementioned $C_{3-8}$ carbocyclyl groups as well as octahydro-lH indenyl, decahydronaphthalenyl, spiro[4.5]decanyl and the like.

As used herein, the term "δ" refers to delta (ppm).

As used herein, the term "DMSO" refers to dimethylsulfoxide.

As used herein, the term "halo" or "halogen" employed alone or as part of another substituent means, unless otherwise stated, a fluorine, chlorine, bromine, or iodine atom, such as fluorine, chlorine, or bromine, further such as, fluorine or chlorine.

As used herein, the term "heterocycle", by itself or as part of another substituent means, unless otherwise stated, an unsubstituted or substituted, stable, mono- or multi-cyclic heterocyclic ring system that consists of carbon atoms and at least one heteroatom. A heterocycle refers to any 3- to 18-membered non-aromatic radical monocyclic or polycyclic moiety comprising at least one heteroatom selected from nitrogen, oxygen, phosphorous and sulfur. In some aspects, the heteroatom(s) are chosen from N, O, and S. A heterocyclyl group can be a monocyclic, bicyclic, tricyclic or tetracyclic ring system, wherein the polycyclic ring systems can be a fused, bridged or spiro ring system. Heterocyclyl polycyclic ring systems can include one or more heteroatoms in one or both rings. A heterocyclyl group can be saturated or partially unsaturated. Partially unsaturated heterocycloalkyl groups can be termed "heterocycloalkenyl" if the heterocyclyl contains at least one double bond, or "heterocycloalkynyl" if the heterocyclyl contains at least one triple bond. Whenever it appears herein, a numerical range such as "5 to 18" refers to each integer in the given range; e.g., "5 to 18 ring atoms" means that the heterocyclyl group can consist of 5 ring atoms, 6 ring atoms, etc., up to and including 18 ring atoms.

An N-containing heterocyclyl moiety refers to an non-aromatic group in which at least one of the ring atoms is a nitrogen atom. The heteroatom(s) in the heterocyclyl radical can be optionally oxidized. One or more nitrogen atoms, if present, can be optionally quaternized. Heterocyclyl also includes ring systems substituted with one or more nitrogen oxide (-0-) substituents, such as piperidinyl N-oxides. The heterocyclyl is attached to the parent molecular structure through any atom of any of the ring(s).

"Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment to the parent molecular structure is on the heterocyclyl ring. In some embodiments, a heterocyclyl group is a 5-14 membered non-aromatic ring system having ring carbon atoms and 1-4 ring heteroatoms, wherein each heteroatom is independently selected from nitrogen, oxygen, phosphorous and sulfur ("5-14 membered heterocyclyl"). In some embodiments, a heterocyclyl group is a 3-10 membered non-aromatic ring system having ring carbon atoms and 1-4 ring heteroatoms, wherein each heteroatom is independently selected from nitrogen, oxygen, phosphorous and sulfur ("3-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, phosphorous and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, phosphorous and sulfur ("5-6 membered heterocyclyl"). In some embodiments, the 5-6 membered heterocyclyl has 1-3 ring heteroatoms selected from nitrogen, oxygen phosphorous and sulfur. In some embodiments, the 5-6 membered heterocyclyl has 1-2 ring heteroatoms selected from nitrogen, oxygen, phosphorous and sulfur. In some embodiments, the 5-6 membered heterocyclyl has 1 ring heteroatom selected from nitrogen, oxygen, phosphorous and sulfur.

Exemplary 3-membered heterocyclyls containing 1 heteroatom include, without limitation, azirdinyl, oxiranyl, and thiorenyl. Exemplary 4-membered heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2, 5-dione. Exemplary 5-membered heterocyclyls containing 2 heteroatoms include, without limitation, dioxolanyl, oxathiolanyl, thiazolidinyl, and dithiolanyl. Exemplary 5-membered heterocyclyls containing 3 heteroatoms include, without limitation, triazolinyl, diazolonyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6 membered heterocyclyl groups containing 2 heteroatoms include, without limitation, piperazinyl, morpholinyl, thiomorpholinyl, dithianyl, dioxanyl, and triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, benzoxanyl, benzopyrrolidinyl, benzopiperidinyl, benzoxolanyl, benzothiolanyl, benzothianyl, tetrahydroindolyl, tetrahydroquinolinyl, tetrahydroisoquinolinyl, decahydroquinolinyl, decahydroisoquinolinyl, 3-1H-benzimidazol-2-one, (1-substituted)-2-oxo-benzimidazol-3-yl, octahydrochromenyl, octahydroisochromenyl, decahydronaphthyridinyl, decahydro-1,8-naphthyridinyl, octahydropyrrolo[3,2-b]pyrrole, phenanthridinyl, indolinyl, phthalimidyl, naphthalimidyl, chromanyl, chromenyl, 1H-benzo[e] [1,4]diazepinyl, 1,4,5,7-tetrahydropyrano[3,4-b]pyrrolyl, 5,6-dihydro-4H-furo[3,2-b]pyrrolyl, 6,7-dihydro-5H-furo [3,2-b]pyranyl, 5,7-dihydro-4H-thieno [2,3-c]pyranyl, 2,3-dihydro-1H-pyrrolo[2,3-b]pyridinyl, hydrofuro[2,3-b]pyridinyl, 4,5,6,7 tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztnazolyl, thioxanthinyl, carbazolyl, carbolinyl, acridinyl, pyrrolizidinyl, and quinolizidinyl.

As used herein, the term "heteroaryl" or "heteroaromatic", by itself or as part of another substituent means, unless otherwise stated, a 5-18 membered monocyclic or polycyclic (e.g., bicyclic or tricyclic) aromatic ring system (e.g., having 6, 10 or 14 t electrons shared in a cyclic array) having ring carbon atoms and 1-6 ring heteroatoms provided in the aromatic ring system, wherein each heteroatom is independently selected from nitrogen, oxygen, phosphorous and sulfur ("5-18 membered heteroaryl"). Heteroaryl polycyclic ring systems can include one or more heteroatoms in one or both rings. Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms. In some instances, a heteroaryl can have 5 to 14 ring atoms.

For example, an N-containing "heteroaryl" or "heteroaromatic" moiety refers to an aromatic group in which at least one of the skeletal atoms of the ring is a nitrogen atom. One or more heteroatom(s) in the heteroaryl radical can be optionally oxidized. One or more nitrogen atoms, if present, can also be optionally quaternized. Heteroaryl also includes ring systems substituted with one or more nitrogen oxide (-O-) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocyclyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, phosphorous, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, phosphorous, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, phosphorous, and sulfur ("5-6 membered heteroaryl"). In some embodiments, the 5-6 membered heteroaryl has 1-3 ring heteroatoms selected from nitrogen, oxygen, phosphorous, and sulfur. In some embodiments, the 5-6 membered heteroaryl has 1-2 ring heteroatoms selected from nitrogen, oxygen, phosphorous, and sulfur. In some embodiments, the 5-6 membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b] [1,4] oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzopyranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno [2,3-d]pyrimidinyl, 5,6-dihydrobenzo[h]quinazolinyl, 5,6-dihydrobenzo[h]cinnolinyl, 6,7-dihydro-5H benzo[6,7]cyclohepta[1,2-c]pyridazinyl, dibenzofuranyl, dibenzothiophenyl, furanyl, furazanyl, furanonyl, furo [3,2-c]pyridinyl, 5,6,7,8,9,10-hexahydrocycloocta[d] pyrimidinyl, 5,6,7,8,9,10-hexahydrocycloocta[d] pyridazinyl, 5,6,7,8,9,10 hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d] pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo [4,5] thieno[2,3-d]pyrimdinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e., thienyl).

Further examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl. The aforementioned listings of heterocyclyl and heteroaryl moieties are intended to be representative and not limiting.

As used herein, the term "isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this disclosure.

Geometric isomers can be represented by the symbol ===== which denotes a bond that can be a single, double or triple bond as described herein. Provided herein are various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of plane of the ring are designated "cis/trans."

"Enantiomers" are a pair of stereoisomers that are non-superimposable mirror images of each other. A mixture of a pair of enantiomers in any proportion can be known as a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, optically substantially pure forms and intermediate mixtures. Optically active (R)- and (S)-isomers can be prepared, for example, using chiral synthons or chiral reagents, or resolved using conventional techniques.

The "enantiomeric excess" or "% enantiomeric excess" of a composition can be calculated using the equation shown below. In the example shown below, a composition contains 90% of one enantiomer, e.g., the S enantiomer, and 10% of the other enantiomer, e.g., the R enantiomer.

$ee=(90-10)/1 00=80\%.$

Thus, a composition containing 90% of one enantiomer and 10% of the other enantiomer is said to have an enantiomeric excess of 80%. Some compositions described herein contain an enantiomeric excess of at least about 50%, about 75%, about 90%, about 95%>, or about 99% of the S enantiomer. In other words, the compositions contain an enantiomeric excess of the S enantiomer over the R enantiomer. In other embodiments, some compositions described herein contain an enantiomeric excess of at least about 50%, about 75%, about 90%, about 95%, or about 99% of the R enantiomer. In other words, the compositions contain an enantiomeric excess of the R enantiomer over the S enantiomer.

For instance, an isomer/enantiomer can, in some embodiments, be provided substantially free of the corresponding enantiomer, and can also be referred to as "optically enriched," "enantiomerically enriched," "enantiomerically pure" and "non-racemic," as used interchangeably herein. These terms refer to compositions in which the percent by weight of one enantiomer is greater than the amount of that one enantiomer in a control mixture of the racemic composition (e.g., greater than 1:1 by weight). For example, an enantiomerically enriched preparation of the S enantiomer means a preparation of the compound having greater than about 50% by weight of the S enantiomer relative to the R enantiomer, such as at least about 75% by weight, further such as at least about 80% by weight. In some embodiments, the enrichment can be much greater than about 80% by weight, providing a "substantially enantiomerically enriched," "substantially enantiomerically pure" or a "substantially non-racemic" preparation, which refers to preparations of compositions which have at least about 85% by weight of one enantiomer relative to other enantiomer, such as at least about 90% by weight, and further such as at least about 95% by weight. In certain embodiments, the compound provided herein is made up of at least about 90% by weight of one enantiomer. In other embodiments, the compound is made up of at least about 95%, about 98% o, or about 99% by weight of one enantiomer.

In some embodiments, the compound is a racemic mixture of (S)- and (R)-isomers. In other embodiments, provided herein is a mixture of compounds wherein individual compounds of the mixture exist predominately in an (S)- or (R)-isomeric configuration. For example, the compound mixture has an (S)-enantiomeric excess of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (S)-enantiomeric excess of greater than about 55% o to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% o to about 99.5%, greater than about 95% to about 99.5%, greater than about 96% to about 99.5% o, greater than about 97% to about 99.5%, greater than about 98% to greater than about 99.5% o, greater than about 99% to about 99.5%, or more. In other embodiments, the compound mixture has an (R)-enantiomeric purity of greater than about 55%, about 60%, about 65%, about 70%, about 75%, about 80%, about 85%, about 90%, about 95%, about 96% o, about 97%, about 98%, about 99%, about 99.5% or more. In some other embodiments, the compound mixture has an (R)-enantiomeric excess of greater than about 55% to about 99.5% o, greater than about 60% to about 99.5%, greater than about 65% to about 99.5%, greater than about 70% to about 99.5%, greater than about 75% to about 99.5%, greater than about 80% o to about 99.5%, greater than about 85% to about 99.5%, greater than about 90% to about 99.5% o, greater than about 95% to about 99.5%, greater than about 96% to about 99.5%, greater than about 97% to about 99.5%, greater than about 98% to greater than about 99.5%, greater than about 99% to about 99.5% or more.

In other embodiments, the compound mixture contains identical chemical entities except for their stereochemical orientations, namely (S)- or (R)-isomers. For example, if a compound disclosed herein has a —CH(R)— unit, and R is not hydrogen, then the —CH(R)— is in an (S)- or (R)-stereochemical orientation for each of the identical chemical entities. In some embodiments, the mixture of identical chemical entities is a racemic mixture of (S)- and (R)-isomers. In another embodiment, the mixture of the identical chemical entities (except for their stereochemical orientations), contain predominately (S)-isomers or predominately (R)-isomers. For example, the (S)-isomers in the mixture of identical chemical entities are present at about 55%, about 60%, about 65%, about 70%, about 75%, about 80%, about 85%, about 90%, about 95%, about 96%, about 97%, about 98%, about 99%, about 99.5%, or more, relative to the (R)-isomers. In some embodiments, the (S)-isomers in the mixture of identical chemical entities are present at an (S)-enantiomeric excess of greater than about 55% to about 99.5% o, greater than about 60%> to about 99.5%, greater than about 65%> to about 99.5%, greater than about 70% to about 99.5%, greater than about 75% to about 99.5%, greater than about 80%) to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

In another embodiment, the (R)-isomers in the mixture of identical chemical entities (except for their stereochemical orientations), are present at about 55%, about 60%, about 65%, about 70%, about 75%, about 80%, about 85%, about 90%, about 95%, about 96%, about 97%), about 98%, about 99%, about 99.5%, or more, relative to the (S)-isomers. In some embodiments, the (R)-isomers in the mixture of identical chemical entities (except for their stereochemical orientations), are present at a (R)-enantiomeric excess greater than about 55%, to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90%) to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

Enantiomers can be isolated from racemic mixtures by any method known to those skilled in the art, including chiral high pressure liquid chromatography (HPLC), the formation and crystallization of chiral salts, or prepared by asymmetric syntheses. See, for example, Enantiomers, Racemates and Resolutions (Jacques, Ed., Wiley Interscience, New York, 1981); Wilen et al., Tetrahedron 33:2725 (1977); Stereochemistry of Carbon Compounds (E. L. Eliel, Ed., McGraw-Hill, N Y, 1962); and Tables of Resolving Agents and Optical Resolutions p. 268 (E. L. E1M, Ed., Univ. of Notre Dame Press, Notre Dame, Ind. 1972).

Optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid. The separation of the mixture of diastereoisomers by crystallization followed by liberation of the optically active bases from these salts affords separation of the isomers. Another method involves synthesis of covalent diastereoisomeric molecules by reacting disclosed compounds with an optically pure acid in an activated form or an optically pure isocyanate. The synthesized diastereoisomers can be separated by conventional means such as chromatography, distillation, crystallization or sublimation, and then hydrolyzed to deliver the enantiomerically enriched compound. Optically active compounds can also be obtained by using active starting materials. In some embodiments, these isomers can be in the form of a free acid, a free base, an ester or a salt.

In certain embodiments, the pharmaceutically acceptable form is a tautomer. As used herein, the term "tautomer" is a type of isomer that includes two or more interconvertible compounds resulting from at least one formal migration of a hydrogen atom and at least one change in valency (e.g., a single bond to a double bond, a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. Exemplary tautomerizations include, but are not limited to, keto-to-enol; amide-to-imide; lactam-to-lactim; enamine-to-imine; and enamine-to-(a different) enamine tautomerizations. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, substitution with heavier isotopes such as deuterium affords greater stability (for example, increased half-life or reduced loading requirements). Isotopically-labeled compounds are prepared by any suitable method or by processes using an appropriate isotopically-labeled reagent in place of the non-labeled reagent otherwise employed.

As used herein, the term "reaction condition" refers to a physical treatment, chemical reagent, or combination thereof, which is required or optionally required to promote a reaction. Non-limiting examples of reaction conditions are electromagnetic radiation, heat, a catalyst, a chemical reagent (such as, but not limited to, an acid, base, electrophile or nucleophile), and a buffer.

As used herein, the term "salt" refers to a salt of a compound contemplated herein, including inorganic acids, organic acids, inorganic bases, organic bases, solvates, hydrates, or clathrates thereof. As used herein, the term "salt" embraces addition salts of free acids or free bases that are compounds useful in the methods described herein. In some cases, undesired salts may nonetheless possess properties such as high crystallinity, which may have utility in the practice of the methods described herein, such as, for example, utility in process of synthesis or purification of compounds described herein.

Suitable acid addition salts may be prepared from an inorganic acid or an organic acid. Examples of inorganic acids include hydrochloric, hydrobromic, hydriodic, nitric, carbonic, sulfuric, phosphoric acids, perchloric and tetrafluoroboronic acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxy-ethanesulfonic, p-toluenesulfonic, sulfanilic, cyclohexylaminosulfonic, stearic, alginic, β-hydroxybutyric, salicylic, galactaric and galacturonic acid. Suitable base addition salts of disclosed compounds include, for example, metallic salts including alkali metal, alkaline earth metal and transition metal salts such as, for example, lithium, calcium, magnesium, potassium, ammonium, sodium and zinc salts. Acceptable base addition salts also include organic salts made from basic amines such as, for example, N,N'-dibenzyl-ethylenediamine, chloroprocaine, choline, diethanolamine, ethylenediamine, meglumine (N-methyl-glucamine) and procaine. All of these salts may be prepared by conventional means from the corresponding free base compound by reacting, for example, the appropriate acid or base with the corresponding free base.

As used herein, the term "substituted" means that an atom or group of atoms has replaced hydrogen as the substituent attached to another group. Unless stated otherwise, any group recited herein may be substituted.

For aryl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_i$-$C_6$ alkyl, —OH, $C_i$-$C_6$ alkoxy, halo, amino, acetamido and nitro. As used herein, where a substituent is an alkyl or alkoxy group, the carbon chain may be branched, straight or cyclic, such as straight.

Throughout this disclosure, various aspects of the disclosure may be presented in a range format. It should be understood that the description in range format is merely for convenience and brevity and should not be construed as an inflexible limitation on the scope of the present claims. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6, and so forth, as well as individual numbers within that range, for example, 1, 2, 2.7, 3, 4, 5, 5.3, and 6. This applies regardless of the breadth of the range.

Compounds and Methods

Provided herein are cinchonium betaine catalysts that can be used to promote imine isomerization in a highly chemoselective and enantioselective manner. In certain embodiments, the catalysts described herein allow for the asymmetric preparation of chiral amines. The present disclosure further includes compositions comprising one or more of the catalysts described herein, and methods of preparing certain organic compounds using these catalysts.

Figure 1B:
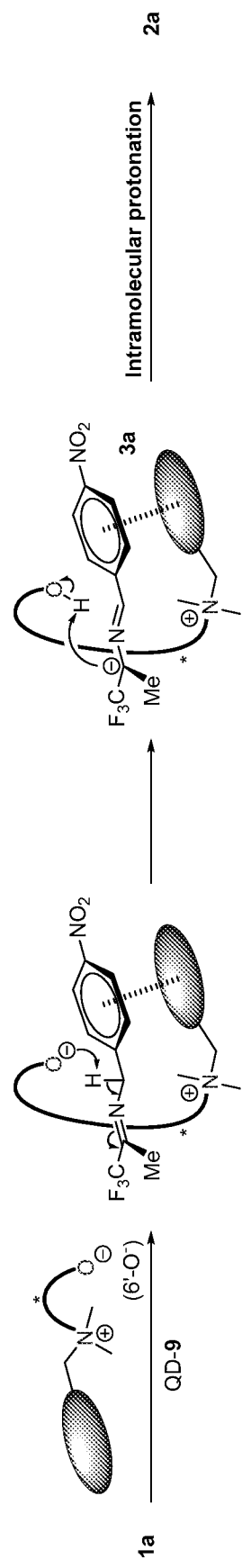
FIG. 1B is a schematic illustration of an imine isomerization reaction. Without wishing to be bound by any theory, the synthetic scheme illustrates 1,3-isomerization of imine 1a using catalyst QD-9 which is an internal zwitterion. The orientation of the positively charged N atom and negatively charged O atom enables greater spatial control of the reaction to provide the desired amine 2a as the sole product.

The present disclosure describes the discovery and development of chiral phase-transfer catalysts that promote highly efficient asymmetric 1,3-imine isomerizations. Modified cinchona alkaloids, such as the quinidine-derived (QD) catalyst QD-9, can promote a highly enantioselective isomerization of trifluoromethyl imines such as 1a (FIG. 1). Without wishing to be limited by any theory, these reactions may proceed through the initial formation of the 2-azaallyl anion 3a, and then a highly enantioselective protonation of 3a to give R-2a. The reaction can be carried out in high yield with as little as about 0.01 mole percent catalyst. These isomerization reactions provide a practical and efficient approach to chiral amino compounds.

TABLE 1

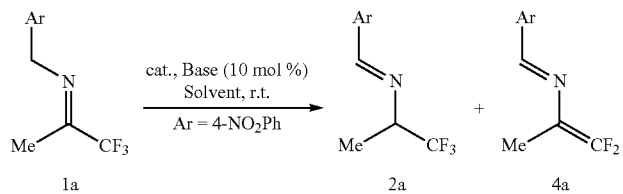

TABLE 1-continued

Catalyst structures: C-5, C-6, C-7, PYR, QD-8, PQD-9a, QD-9a, QD-9b, QD-9c, Q-9c

| Entry | cat. | mol % of cat. | Base | Solvent | t (h) | conv. (%)[a] | ee (%)[b] | 2a/4a[b] |
|---|---|---|---|---|---|---|---|---|
| 1 | C-5 | 0.5 | KOH | Toluene/CHCl₃ = 7/3 | 4 | 16 | −22 | 61/39 |
| 2 | C-6 | 0.5 | KOH | Toluene/CHCl₃ = 7/3 | 4 | 9 | −26 | 45/55 |
| 3 | C-7 | 0.5 | KOH | Toluene/CHCl₃ = 7/3 | 4 | 10 | −12 | 40/60 |
| 4 | QD-9a | 0.5 | KOH | Toluene/CHCl₃ = 7/3 | 4 | 100 | 92 | 98/2 |
| 5 | QD-8 | 0.5 | KOH | Toluene/CHCl₃ = 7/3 | 4 | 10 | −33 | 34/66 |

[a]Reactions were run with 1a (0.025 mmol), aqueous KOH (0.3 μL, 50 wt %, 10 mol %) and catalyst in toluene/CHCl₃ (7/3 v/v, 0.25 mL) at room temperature
[b]Determined by HPLC analysis.

In some embodiments, PQD-10a was used as a precursor of the cinchonium betaine catalyst QD-9a, which could be formed in situ via deprotonation of the PQD-9a by KOH (Table 1). Initially, betaine QD-9a was examined for the isomenzations of 1a under the same conditions as those applied to catalysts C5-C7, which have an unsubstituted quinine bicycle. The isomerization of 1a went to completion in four hours with 0.5 mol % of QD-9a to afford the desired chiral amine R-2a in 92% ee (entry 4, Table 1). In contrast, the quinidine-derived cinchonium salt QD-8, which has a 6-methoxy substituent on the quinine bicycle afforded poor chemoselectivity and enantioselectivity, suggesting that the phenoxide of QD-9a resulted in efficient promotion of the enantioselective isomerization.

TABLE 2

| Entry | cat. | mol % of cat. | Base presented in the reaction | Solvent | t (h) | conv. (%)[b] | ee (%)† | 2a/4a[b] |
|---|---|---|---|---|---|---|---|---|
| 6 | QD-9a | 0.5 | No | Toluene/CHCl₃ = 7/3 | 4 | 76 | 92 | >99/1 |
| 7 | QD-9b | 0.5 | No | Toluene/CHCl₃ = 7/3 | 4 | 97 | 93 | >99/1 |
| 8 | QD-9c | 0.5 | No | Toluene/CHCl₃ = 7/3 | 4 | 98 | 95 | >99/1 |
| 9 | QD-9c | 0.2 | No | Toluene/CHCl₃ = 7/3 | 24 | 77 | 95 | >99/1 |

TABLE 2-continued

| Entry | cat. | mol % of cat. | Base presented in the reaction | Solvent | t (h) | conv. (%)[b] | ee (%†) | 2a/4a[b] |
|---|---|---|---|---|---|---|---|---|
| 10 | QD-9c | 0.2 | solid K$_2$CO$_3$ | Toluene/CHCl$_3$ = 7/3 | 12 | 100 | 95 | >99/1 |
| 11 | QD-9c | 0.02 | solid K$_2$CO$_3$ | Toluene | 24 | 100 | 96[e] | >99/1 |
| 12 | QD-9c | 0.01 | solid K$_2$CO$_3$ | Toluene | 24 | 97 | 96 | >99/1 |
| 13 | Q-9c | 0.05 | solid K$_2$CO$_3$ | Toluene | 24 | 100 | −93 | >99/1 |

[a]Betaine catalysts QD-9 and Q-9c were preformed from treatment of the corresponding precursors PQD-9 and PQ-9c with base.
Reactions were run with 1a (0.025 mmol) in 0.25 mL solvent.
[^]Determined by HPLC analysis.
[e]Absolute configuration was determined to be R.

Further studies using related catalysts (entries 7-8, Table 2) increased the efficiency of the isomerization, for example, using betaine QD-9c gave product R-2a in 98% conversion and 95% ee. Isomerization reactions were also carried out using preformed betaine QD-9c under base free conditions. Specifically, PQD-9c was treated with solid KOH in toluene/CHCb for 15 minutes, when PQD-9c was shown by $^1$H NMR analysis to be converted into the betaine QD-9c. Then the QD-9c solution in toluene/CHCl$_3$ was added to a solution of imine 1a in toluene/CHCl$_3$. After four hours the isomerization was shown to proceed to 98% conversion to afford R-2a in 95% ee (entry 8, Table 2).

The presence of a solid base such as K$_2$CO$_3$ was instrumental for maintaining the activity of the betaine catalyst (entry 10 vs. 9, Table 2). Upon optimizations of solvent, a highly enantioselective isomerization of 1a was performed in 24 hours in toluene with only 0.02 mol % of QD-9c (entry 10, Table 2). The conversion only decreased slightly with 0.01 mol % of QD-9c without compromising enantioselectivity; reaching 97% in 24 hours. For the opposite enantiomer S-2a, a highly enantioselective isomerization of 1a into S-2a could be accomplished with 0.05 mol % of quinine-derived betaine Q-9c (entry 13, Table 2). Thus, the cinchonium betaine catalysts provide catalyst efficiency and the advantage of useful access to either R or S enantiomer of the trifluoromethylated amines 2.

TABLE 3

| Entry | 1 | R | T (° C.) | cat. | mol % of cat. | Yield (%)[b] | ee (%)[c] |
|---|---|---|---|---|---|---|---|
| 1 | 1a | Me | r.t. | QD-9c (Q-9c) | 0.02 (0.05) | 96 (96) | 96 (−93) |
| 2 | 1b | Et | r.t. | QD-9c (Q-9c) | 0.08 (0.10) | 98 (97) | 95 (−91) |
| 3 | 1c | n-Bu | r.t. | QD-9c (Q-9c) | 0.10 (0.20) | 97 (96) | 96 (−90) |
| 4 | 1d[d] | Cyclohexyl | r.t. | QD-9c (Q-9c) | 0.50 (0.50) | 97 (74) | 94 (−86) |
| 5 | 1e | trans-Styryl | 0 | QD-9c (Q-9c) | 0.40 (0.40) | 97 (96) | 95 (−85) |
| 6 | 1f | Ph | 0 | QD-9c (Q-9c) | 0.10 (0.10) | 96 (96) | 90 (−81) |
| 7 | 1g | 4-Me-C$_6$H$_4$ | 0 | QD-9c (Q-9c) | 0.10 (0.10) | 99 (97) | 93 (−85) |
| 8 | 1h | 3-Me-C$_6$H$_4$ | 0 | QD-9c (Q-9c) | 0.10 (0.10) | 98 (98) | 93 (−84) |
| 9 | 1i | 4-OMe-C$_6$H$_4$ | 0 | QD-9c (Q-9c) | 0.10 (0.10) | 99 (96) | 93 (−84) |
| 10 | 1j | 4-F-C$_6$H$_4$ | −20 | QD-9c (Q-9c) | 0.20 (0.05) | 97 (95) | 90 (−79) |

[a]Betaine catalysts QD-9c and Q-9c were performed from treatment of the corresponding precursors PQD-9c and PQ-9 with base.
Reactions were run with 1 (0.2 mmol) in toluene (2.0 mL).
Results in parentheses were obtained with Q-9c.
[^]Isolated yield. determined by FlPLC analysis.
[d]An E/Z mixture of imine stereoisomers (E/Z = 3.2/1) was used.

The scope of imine substrate 1 was investigated with catalysts QD-9c and Q-9c. High enantioselectivity was observed with a variety of aliphatic trifluoromethyl imines of varying length (1a-1c), which were isomerized with QD-9c in 0.02-0.10 mol % loading (entries 1-3, Table 3). For the sterically more hindered cyclohexyl trifluoromethyl imine 1d, a catalyst loading of 0.50 mol % was required in order to achieve a highly enantioselective isomerization in 24 hours (entry 4, Table 3). In addition, QD-9c promoted an isomerization of α,β-unsaturated imine 1e in excellent enantioselectivity and yield, without the formation of the 1,3-proton transfer product. For aryl trifluoromethyl imines (entries 6-10, Table 3), a loading of 0.10 mol % of QD-9c was sufficient to afford a highly enantioselective isomerization of imines 1 within 24 hours to generate the corresponding optically active chiral aryl trifluoromethylated amine 2 in close to quantitative yields. Importantly, isomerizations with betaine Q-9c in similarly low loading afforded the opposite enantiomer of the chiral trifluoromethylated amine in high optical purities and yields (Table 3). The time necessary for reaction completion indicates that the catalyst turnover rate is high compared to other known catalyst-based imine isomerizations.

These isomerization reactions are quite clean in that side products and reagent-based components are easily separated from the amine 2 product. For example, a simple filtration of the reaction mixture through a plug of deactivated silica gel followed by solvent removal furnished amine 2 in pure form as determined by NMR analysis. Amine products such as 2 can be further reduced to afford the chiral amine 2b using NaBH$_4$ or other suitable hydride reductants as shown below, followed by treatment with acid.

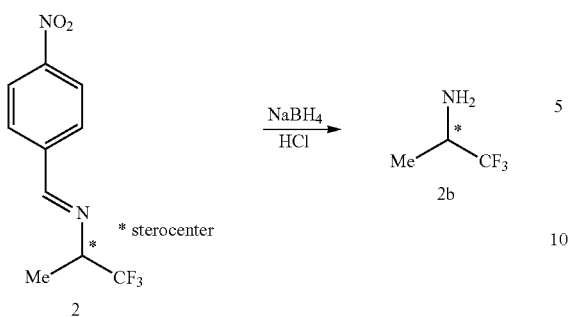

These studies demonstrate that a broad range of alkyl, alkenyl and aryl trifluoromethyl imines can be converted in a highly enantioselective manner into either enantiomers of the corresponding optically active trifluoromethylated amines with about 0.02 to about 0.10 mol % of the cinchonium betaine catalysts. With an accessible operational protocol and low catalyst loading, the transformations disclosed herein also provide a practical method for organic synthesis.

Provided herein is a compound, or a salt, tautomer, enantiomer or diastereoisomer thereof, of formula (I):

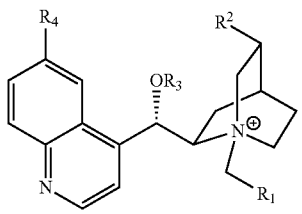

wherein:

$R^1$ is

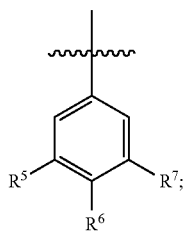

$R^5$ and $R^7$ are independently aryl;

$R^6$ is alkoxy or alkylsiloxy;

$R^2$ is alkenyl;

$R^3$ is optionally substituted heteroaryl, where each optional substituent is independently selected from aryl and halo; and $R^4$ is —OH or —O⁻.

In some embodiments, $R_5$ and $R_7$ are each phenyl. In some embodiments, $R_6$ is selected from methoxy, t-butoxy and t-butyldimethylsiloxy. In some embodiments, $R_2$ is —CH=CH$_2$. In some embodiments, $R_3$ is pyrimidinyl substituted with one or more groups selected from aryl and halo. For example, $R_3$ can be 4-chloro-2,5-diphenylpyrimidinyl (PYR). In some embodiments, $R_4$ is —OH while in other embodiments, $R_4$ is —O⁻.

In certain embodiments, the compound is at least one selected from:

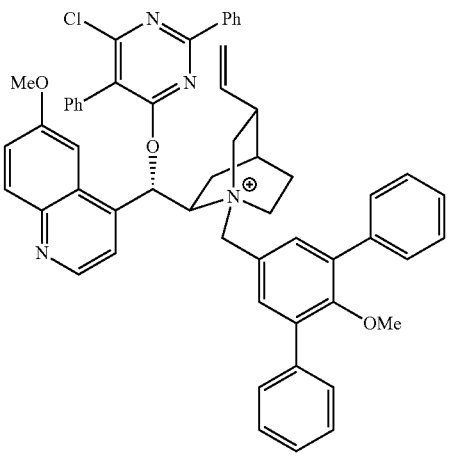 [SMILES: C=CC1C[N+]2(Cc3cc(-c4ccccc4)c(OC)c(-c4ccccc4)c3)CCC1CC2[C@@H](Oc1nc(-c2ccccc2)nc(Cl)c1-c1ccccc1)c1ccnc2ccc(OC)cc12]

(1,S',2R,4,S',5R)-2-((,S)-((6-chloro-2,5-diphenylpyrimidin-4-yl)oxy)(6-methoxyquinolin-4-yl)methyl)-1-((2'-methoxy-[1,1':3',1"-terphenyl]-5'-yl)methyl)-5-vinylquinuclidin-1-ium (QD-8)

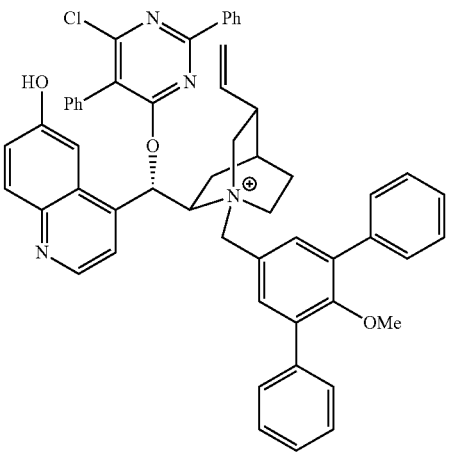

(1S,2R,4S,5R)-2-((,S)-((6-chloro-2,5-diphenylpyrimidin-4-yl)oxy)(6-hydroxyquinolin-4-yl)methyl)-1-((2'-methoxy-[1,1':3',1"-terphenyl]-5'-yl)methyl)-5-vinylquinuclidin-1-ium (PQD-9)

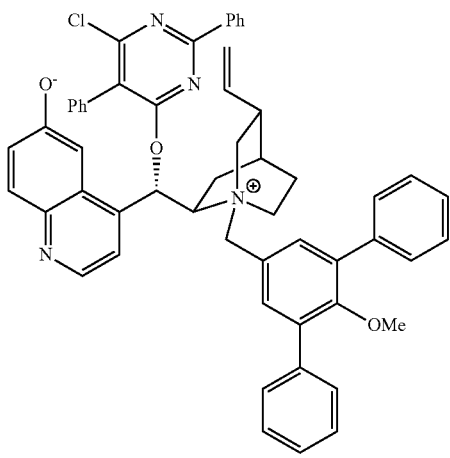

4-((5)-((6-chloro-2,5-diphenylpyrimidin-4-yl)oxy)((1^R, 4^5R)-1-((2'-methoxy-[1,Γ:3',Γ'-terphenyl]-5'-yl)methyl)-5-vinylquinuclidin-1-ium-2-yl)methyl)quinolin-6-olate (QD-9a)

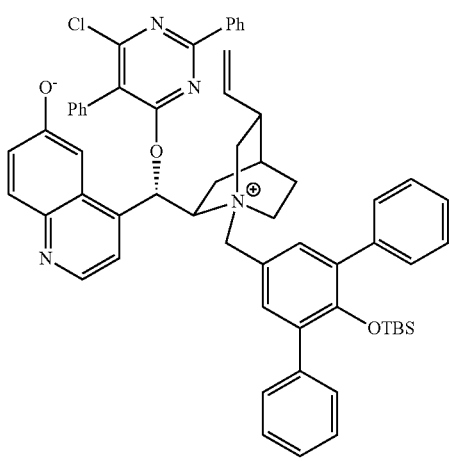 [SMILES: C=CC1C[N+]2(Cc3cc(-c4ccccc4)c(O[Si](C)(C)C(C)(C)C)c(-c4ccccc4)c3)CCC1CC2[C@@H](Oc1nc(-c2ccccc2)nc(Cl)c1-c1ccccc1)c1ccnc2ccc([O-])cc12]

4-((S)-((1S,2R,4S,5R)-1-((2H(tert^^ldimethylsilyl)oxy)-[1,1':3',1"-terphenyl]-5'-yl)methyl)-5-vinylquinuclidin-14um-2-yl)((6-chloro-2,5-diphenylpyrimidin-4-yl)oxy)methyl)quinolin-6-olate (QD-9b)

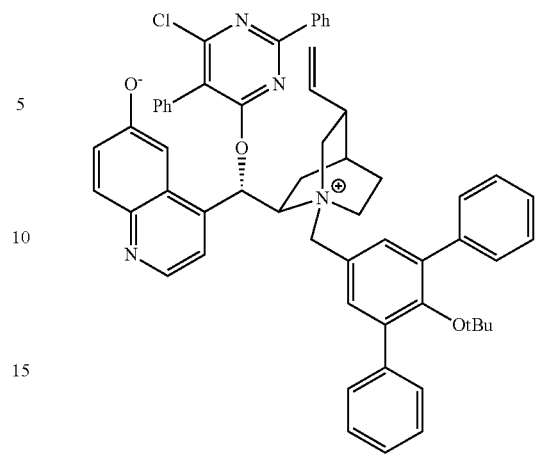

4-((S)-((1S,2R,4^5R)-1-((2'-(tert-butoxy)-[1,r:3',r'-terphenyl]-5'-yl)methyl)-5-vinylquinuclidin-14um-2-yl)((6-chloro-2,5-diphenylpyrimidin-4-yl)oxy)methyl)quinolin-6-olate (QD-9c) and

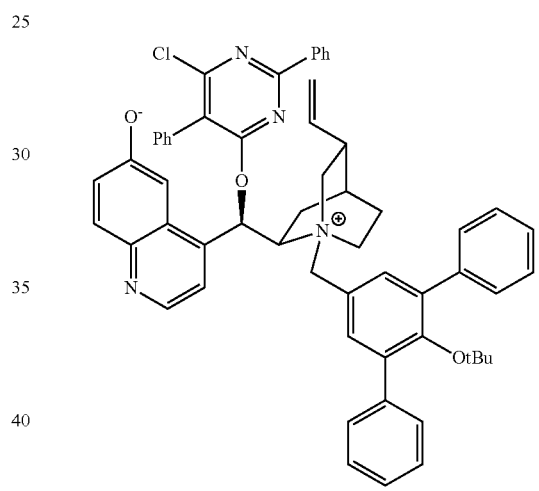

4-((R)-((1^2 R,4^5 R)-1-((2'<tert-butoxy)-[1,1^3 ',r'-terphenyl]-5'-yl)methyl)-5-vinylquinuclidin-14um-2-yl)((6-chloro-2,5-diphenylpyrimidin-4-yl)oxy)methyl)quinolin-6-olate (Q-9c).

Provided herein is a method of promoting imine isomerization that comprises contacting the imine with at least one compound disclosed herein, wherein the imine comprises formula (II):

wherein:

$R^a$ is selected from optionally substituted alkyl, optionally substituted aryl, optionally substituted cycloalkyl, and optionally substituted alkenyl, where each optional substituent is independently selected from alkyl, alkoxy, and halo;

$R^b$ is trifluoromethyl; and
$R^c$ is aryl;
to afford a compound a compound of formula (III)

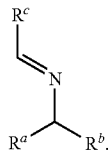
(III)

In some embodiments, $R^a$ is alkyl, such as methyl, ethyl and n-butyl. In other embodiments, $R^a$ is cycloalkyl, such as cyclohexyl. In some embodiments, $R^a$ is trans-styryl. In some embodiments, $R^a$ is phenyl, optionally substituted with methyl, methoxy or fluoro. In some embodiments, $R^c$ is phenyl substituted with a nitro group.

In certain embodiments, the imine and the at least one compound are contacted in a non-aqueous system in the presence of a base. In some embodiments, the base is a hydroxide, such as NaOH or KOH. In other embodiments, the base can be a carbonate base, such as $Na_2CO_3$ or $K_2CO_3$. The amount of base in the system can be catalytic, such as about 10 mol %.

In some embodiments, the amount of the at least one compound in the system ranges from about 0.01 mol % to about 5 mol % with respect to the imine, such as about 0.01 mol % to about 0.1 mol %, such as about 0.05 mol % to about 1 mol %, such as about 0.1 mol % to about 0.5 mol %. In some embodiments, the amount of the at least one compound in the system is selected from about 0.01 mol %, about 0.02 mol %, about 0.05 mol %, about 0.08 mol %, about 0.1 mol %, about 0.2 mol %, about 0.3 mol %, about 0.4 mol %, and about 0.5 mol %.

Those skilled in the art will recognize, or be able to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The following examples are put forth so as to provide those of ordinary skill in the art with a complete disclosure and description of how to make and use the assay, screening, and methods, and are not intended to limit the scope of what the inventor(s) regard(s) as the invention.

EXAMPLES

The compounds disclosed herein may be synthesized using techniques well-known in the art of organic synthesis. The starting materials and intermediates required for the synthesis may be obtained from commercial sources, and/or synthesized according to methods known to those skilled in the art and/or disclosed elsewhere herein.

The following Examples are provided for the purpose of illustration only, and the disclosure is not limited to these Examples, but rather encompasses all variations that are evident as a result of the teachings provided herein.

Materials and Methods 1H and $^{13}C$ NMR spectra were recorded on a Varian instrument (400 MHz and 100 MHz, respectively). 1H NMR spectra were internally referenced to tetramethylsilane signal, $^{13}C$ NMR spectra were internally referenced to $CDCl_3$ signal (δ=77.0 ppm) or CD3OD signal (δ=48.4 ppm) and $^{19}F$ NMR spectra were internally referenced to $CF_3COOH$ (δ=−76.55 ppm). Data for 1H spectra and $^{19}F$ are recorded as follows: chemical shift (δ, ppm), multiplicity (s, singlet; d, doublet; t, triplet; q, quartet; m, multiplet), integration, coupling constant (Hz). Data for $^{13}C$ NMR are reported in terms of chemical shift (δ, ppm). Infrared spectra were recorded on a Perkin Elmer FT-IR Spectrometer and are reported in frequency of absorption ($cm^{-1}$). Low resolution and high resolution mass spectra were recorded on either a Micromass 70-VSE-B instrument (EI, CI) or a Micromass Q-TOF instrument (ESI). Specific rotations were measured on a Jasco Digital Polarimeter. High performance liquid chromatography (HPLC) analyses were performed on a Hewlett-Packard 1100 Series instrument equipped with a quaternary pump, using Daicel Chiralpak AD, Daicel Chiralcel OJ-H or AS-H Columns (250×4.6 mm). UV absorption was monitored at 254 nm.

Example 1: Catalysts

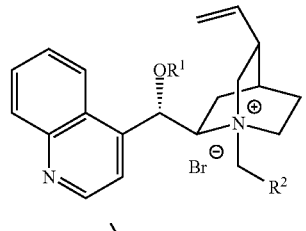

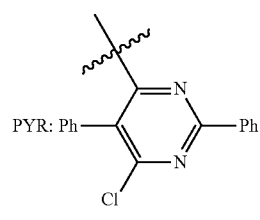

C-5 $R^1$ = Bn, $R^2$ = Ph
C-6 $R^1$ = PYR, $R^2$ = Ph

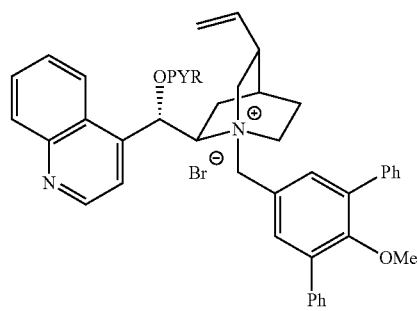

C-7

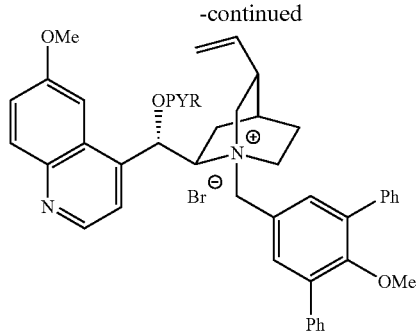
QD-8
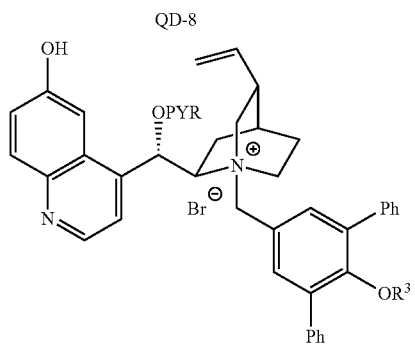
PQD-9a R³ = Me
PQD-9b R³ = TBS
PQD-9c R³ = tBu
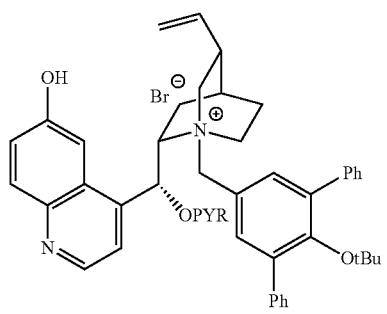
PQ-9c
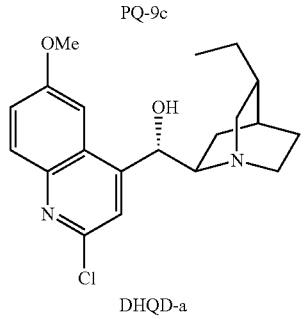
DHQD-a
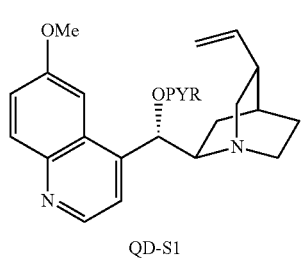
QD-S1
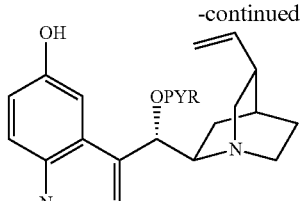
QD-S2
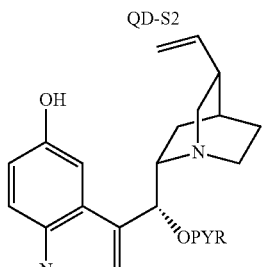
QD-S2
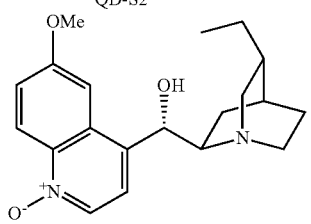
DHQD-S3
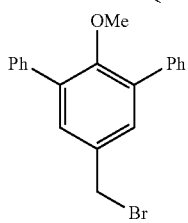
S-4
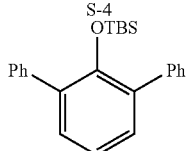
S-5
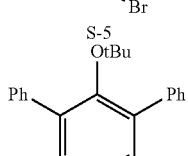
S-6
Structures of Catalysts, Tertiary Amine Precursors and Aryl Bromides
Catalyst C-5 was prepared according to Santoro et al. *Chem. Commun.* 2007, 5155. Catalysts C-6 and C-7 were prepared according to Wu et al. *Nature* 2015, 523, 445. Tertiary amine precursor QD-S1 was prepared according to Provencher et al. *Angew. Chem. Int. Ed.* 2011, 50, 10565. Tertiary amine precursors QD-S2 and Q-S2 were prepared according to Wu et al. Angew. Chem. Int. Ed. 2006, 45, 4301. Tertiary amine precursor DHQD-S3 was prepared according to Wu et al. *Am. Chem. Soc.* 2011, 133, 12458. Benzyl bromides S-4, S-5 and S-6 were prepared according to Wu 2015.

Preparation of Catalyst DHQD-a

General Procedure for the Preparation of Catalysts QD-8, PQD-9a to 9c and PQ-9c

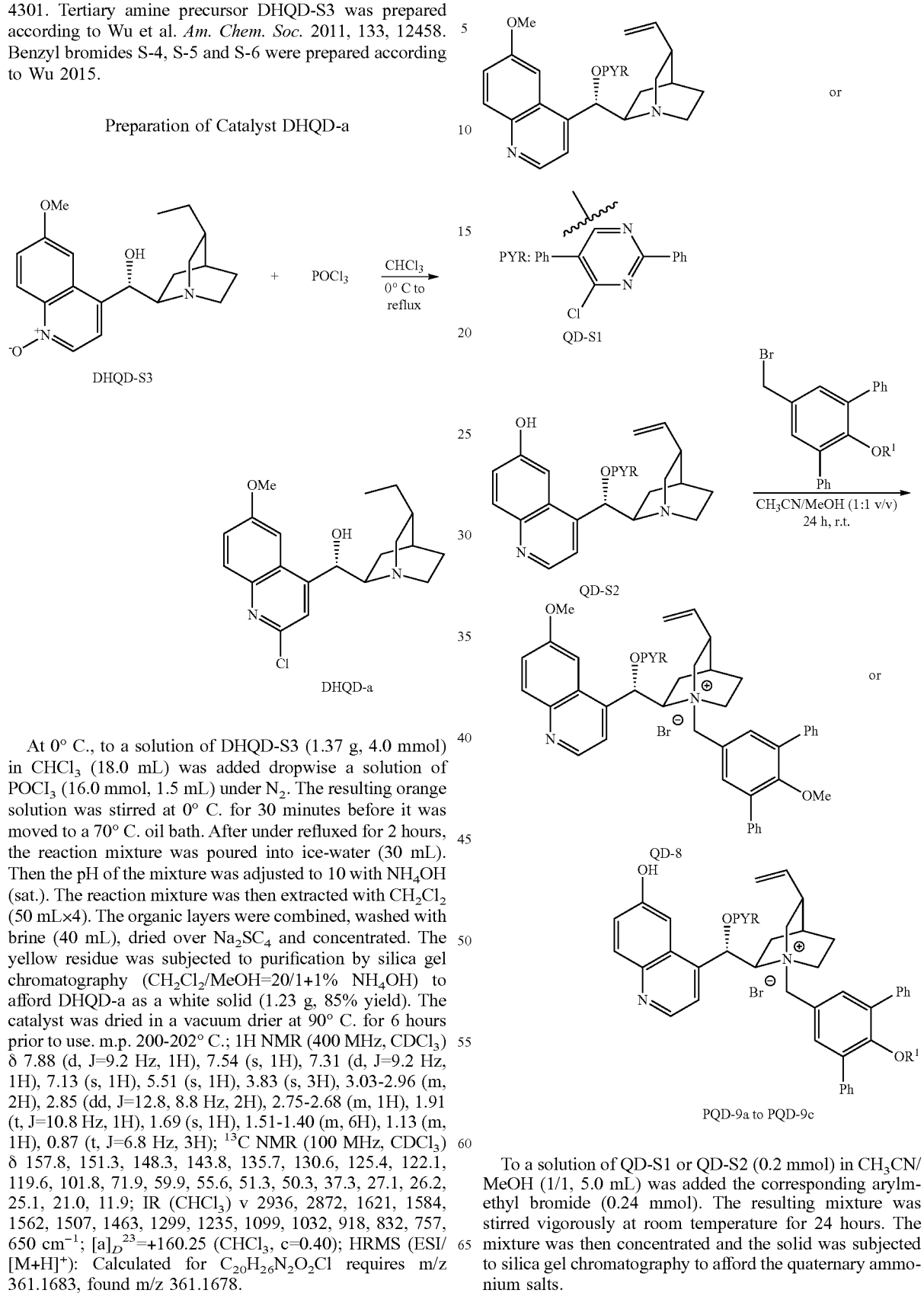

At 0° C., to a solution of DHQD-S3 (1.37 g, 4.0 mmol) in CHCl$_3$ (18.0 mL) was added dropwise a solution of POCl$_3$ (16.0 mmol, 1.5 mL) under N$_2$. The resulting orange solution was stirred at 0° C. for 30 minutes before it was moved to a 70° C. oil bath. After under refluxed for 2 hours, the reaction mixture was poured into ice-water (30 mL). Then the pH of the mixture was adjusted to 10 with NH$_4$OH (sat.). The reaction mixture was then extracted with CH$_2$Cl$_2$ (50 mL×4). The organic layers were combined, washed with brine (40 mL), dried over Na$_2$SO$_4$ and concentrated. The yellow residue was subjected to purification by silica gel chromatography (CH$_2$Cl$_2$/MeOH=20/1+1% NH$_4$OH) to afford DHQD-a as a white solid (1.23 g, 85% yield). The catalyst was dried in a vacuum drier at 90° C. for 6 hours prior to use. m.p. 200-202° C.; 1H NMR (400 MHz, CDCl$_3$) δ 7.88 (d, J=9.2 Hz, 1H), 7.54 (s, 1H), 7.31 (d, J=9.2 Hz, 1H), 7.13 (s, 1H), 5.51 (s, 1H), 3.83 (s, 3H), 3.03-2.96 (m, 2H), 2.85 (dd, J=12.8, 8.8 Hz, 2H), 2.75-2.68 (m, 1H), 1.91 (t, J=10.8 Hz, 1H), 1.69 (s, 1H), 1.51-1.40 (m, 6H), 1.13 (m, 1H), 0.87 (t, J=6.8 Hz, 3H); $^{13}$C NMR (100 MHz, CDCl$_3$) δ 157.8, 151.3, 148.3, 143.8, 135.7, 130.6, 125.4, 122.1, 119.6, 101.8, 71.9, 59.9, 55.6, 51.3, 50.3, 37.3, 27.1, 26.2, 25.1, 21.0, 11.9; IR (CHCl$_3$) ν 2936, 2872, 1621, 1584, 1562, 1507, 1463, 1299, 1235, 1099, 1032, 918, 832, 757, 650 cm$^{-1}$; [a]$_D^{23}$=+160.25 (CHCl$_3$, c=0.40); HRMS (ESI/ [M+H]$^+$): Calculated for C$_{20}$H$_{26}$N$_2$O$_2$Cl requires m/z 361.1683, found m/z 361.1678.

To a solution of QD-S1 or QD-S2 (0.2 mmol) in CH$_3$CN/MeOH (1/1, 5.0 mL) was added the corresponding arylmethyl bromide (0.24 mmol). The resulting mixture was stirred vigorously at room temperature for 24 hours. The mixture was then concentrated and the solid was subjected to silica gel chromatography to afford the quaternary ammonium salts.

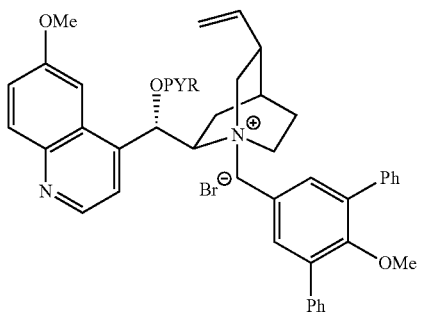

QD-8

Catalyst QD-8 was isolated by flash chromatography (CH$_2$Cl$_2$/MeOH=80/1 to CH$_2$Cl$_2$/MeOH=40/1) as a yellowish solid in 63% yield. Decomposed at 163° C.; 1H NMR (400 MHz, CDCl$_3$) δ 8.75 (d, J=4.4 Hz, 1H), 8.04 (d, J=9.2 Hz, 2H), 7.85-7.36 (m, 24H), 7.20 (t, J=7.6 Hz, 2H), 6.62 (d, J=12 Hz, 1H), 5.91-5.86 (m, 1H), 5.29-4.92 (m, 5H), 4.44 (s, 3H), 4.18 (d, J=12 Hz, 1H), 3.30 (t, J=11.6 Hz, 1H), 3.16 (s, 3H), 3.03 (t, J=10 Hz, 1H), 2.90 (q, J=10.8 Hz, 1H), 2.40-2.30 (m, 2H), 2.04-1.94 (m, 2H), 1.79-1.73 (m, 1H), 1.47-1.40 (m, 1H); $^{13}$CNMR (100 MHz, CDCl$_3$) δ 164.7, 163.2, 161.4, 159.6, 156.9, 146.2, 145.0, 137.1, 136.7, 135.5, 134.9, 132.0, 129.5, 129.3, 129.1, 128.5, 128.4, 127.8, 122.4, 102.1, 72.2, 64.5, 60.9, 60.5, 57.6, 55.9, 54.7, 38.3, 27.4, 23.5, 23.3; IR (CHCl$_3$) ν 2937, 2360, 2335, 2314, 2254, 1573, 1515, 1409, 1354, 1216, 1002, 744, 699, 664 cm$^{-1}$; [a]$_D^{23}$=−71.50 (CHCl$_3$, c=0.40); HRMS (ESI/[M-Br$^-$]$^+$): Calculated for C$_{56}$H$_{50}$ClN$_4$O$_3$ requires m/z 861.3566, found m/z 861.3555.

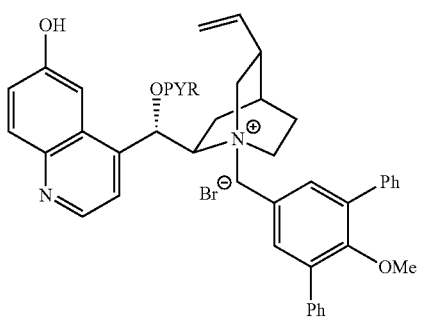

PQD-9a

Catalyst PQD-9a was isolated by flash chromatography (CH$_2$Cl$_2$/MeOH=100/1 to CH$_2$Cl$_2$/MeOH=40/1) as a reddish solid in 48% yield. Decomposed at 193° C.; 1H NMR (400 MHz, CDCl$_3$) δ 8.68 (s, 1H), 8.64 (d, J=4.4 Hz, 1H), 8.06 (d, J=9.2 Hz, 1H), 7.85 (d, J=7.2 Hz, 2H), 7.74-7.64 (m, 7H), 7.56-7.35 (m, 13H), 7.22 (t, J=8 Hz, 2H), 7.13 (d, J=4.4 Hz, 1H), 6.47 (d, J=11.6 Hz, 1H), 5.12-4.96 (m, 4H), 4.73 (t, J=9.6 Hz, 1H), 4.24 (d, J=11.6 Hz, 1H), 3.37 (t, J=11.2 Hz, 1H), 3.14 (s, 3H), 3.03 (m, 2H), 2.31 (q, J=6 Hz, 1H), 2.14 (t, J=12.4 Hz, 1H), 1.95-1.91 (m, 2H), 1.79 (m, 1H), 0.72-0.70 (m, 1H); $^{13}$C NMR (100 MHz, CDCl$_3$) δ 164.7, 163.3, 161.7, 157.7, 157.0, 156.9, 146.0, 143.8, 137.0, 136.8, 131.7, 129.6, 129.3, 129.2, 128.7, 128.6, 128.3, 127.9, 104.8, 72.3, 65.3, 65.1, 61.8, 60.5, 56.6, 54.4, 38.3, 35.6, 27.2, 23.7, 23.4, 23.3, 22.6, 12.0, 11.6; IR (CHCl$_3$) ν 3746, 3354, 3063, 2952, 2359, 2334, 1619, 1574, 1516, 1410, 1227, 1001, 755, 702 cm$^{-1}$; [a]$_D^{23}$=−89.66 (CHCl$_3$, c=0.29); HRMS (ESI/[M-Br$^-$]$^+$): Calculated for C$_{55}$H$_{48}$ClN$_4$O$_3$ requires m/z 847.3409, found m/z 847.3403.

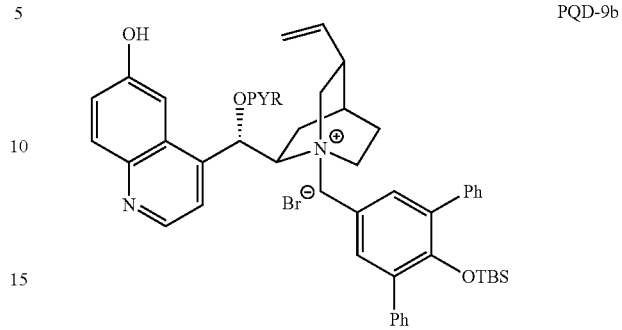

PQD-9b

Catalyst PQD-9b was isolated by flash chromatography (EtOAc/HCOOH=100/0.1) as a brown solid in 57% yield. Decomposed at 192° C.; 1H NMR (400 MHz, CDCl$_3$) δ 9.45z (s, 1H), 8.71 (s, 1H), 8.63 (d, J=4.4 Hz, 1H), 8.06 (d, J=9.2 Hz, 1H), 7.86 (d, J=8 Hz, 2H), 7.72-7.62 (m, 6H), 7.56-7.37 (m, 13H), 7.23 (t, J=7.2 Hz, 3H), 7.10 (d, J=4.4 Hz, 1H), 6.47 (d, J=12 Hz, 1H), 5.15 (t, J=10.8 Hz, 1H), 5.04-4.89 (m, 4H), 4.73 (t, J=9.2 Hz, 1H), 4.26 (d, J=12 Hz, 1H), 3.36 (t, J=11.2 Hz, 1H), 3.01 (m, 2H), 2.28 (q, J=5.6 Hz, 1H), 2.13 (t, J=12.4 Hz, 1H), 1.96-1.77 (m, 4H), 1.26 (m, 2H), 0.68 (s, 9H), −0.82 (d, J=4 Hz, 6H); $^{13}$CNMR (100 MHz, CDCl$_3$) δ 164.8, 163.4, 161.7, 157.8, 152.1, 145.9, 143.9, 138.4, 137.1, 136.0, 135.6, 134.7, 134.3, 132.2, 131.8, 130.1, 129.6, 129.5, 129.4, 129.3, 129.2, 129.1, 128.9, 128.7, 128.4, 128.3, 127.6, 125.1, 124.1, 119.6, 119, 118.7, 117.7, 104.9, 72.5, 64.9, 61.7, 56.5, 54.4, 38.3, 27.3, 26.0, 25.6, 23.5, 22.6, 18.2, −3.6, −4.7, −4.8; IR (CHCl$_3$) ν 3896, 3864, 3774, 3748, 3608, 3489, 3464, 3170, 3122, 2941, 2586, 2351, 1573, 1515, 1412, 1250, 1222, 1003, 893, 780, 702 cm$^{-1}$; [a]$_D^{23}$=−80.62 (CHCl$_3$, c=0.16); HRMS (ESI/[M-Br$^-$]$^+$): Calculated for C$_6$oH$_6$oClN$_4$O$_3$Si requires m/z 947.4118, found m/z 947.4102.

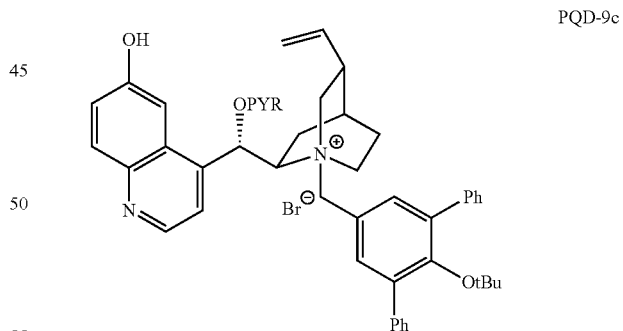

PQD-9c

Catalyst PQD-9c was isolated by flash chromatography (EtOAc/HCOOH=100/0.1) as a reddish solid in 71% yield. Decomposed at 165° C.; $^1$H NMR (400 MHz, CDCl$_3$) δ 9.44 (s, 1H), 8.72 (s, 1H), 8.62 (d, J=4.4 Hz, 1H), 8.06 (d, J=9.2 Hz, 1H), 7.86 (d, J=8 Hz, 2H), 7.71 (s, 1H), 7.60 (d, J=7.6 Hz, 4H), 'I 0.56-1.31 (m, 13H), 7.23 (t, J=8.0 Hz, 3H), 7.10 (d, J=4.4 Hz, 1H), 6.50 (d, J=12.0 Hz, 1H), 5.17 (t, J=10.8 Hz, 1H), 5.04-4.90 (m, 3H), 4.73 (t, J=9.2 Hz, 1H), 4.28 (d, J=12.0 Hz, 1H), 3.35 (t, J=11.2 Hz, 1H), 3.01 (m, 3H), 2.29 (q, J=6.0 Hz, 1H), 2.14 (t, J=11.6 Hz, 1H), 1.93-1.90 (m, 2H), 1.77 (m, 1H), 1.28 (m, 1H), 0.57 (s, 9H); $^{13}$C NMR (100 MHz, CDCl$_3$) δ 169.5, 164.8, 163.3, 161.7, 157.8, 153.6, 134.7, 132.2, 131.8, 131.7, 130.1, 129.5, 129.3, 128.7, 128.4, 127.6, 124.1, 121.4, 119.0, 117.7, 104.9, 84.2, 72.6, 65.0, 61.5, 56.5, 54.4, 38.2, 29.0, 27.2, 23.5, 22.7; IR (CHC13) v 3748, 3406, 3354, 2976, 2336, 1618, 1574, 1515, 141 1, 1362, 1224, 1154, 1002, 756, 702 cm$^{-1}$; [a]$_D^{23}$=−80.59 (CHCl$_3$, c=0.17); HRMS (ESI/[M-Br$^-$]$^+$): Calculated for C$_{58}$H$_{54}$C1N$_4$O$_3$ requires m/z 889.3879, found m/z 889.3869.

PQ-9c

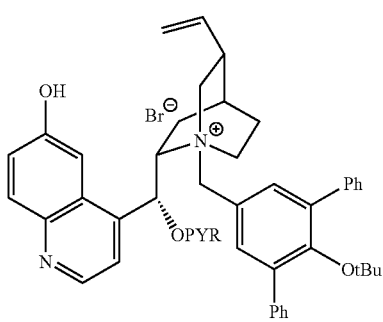

Catalyst PQD-9c was isolated by flash chromatography (EtOAc to EtOAc/MeOH=80/1) as a yellow solid in 45% yield. Decomposed at 170° C.; 1H NMR (400 MHz, CD$_3$OD) δ 8.64 (d, J=4.8 Hz, 1H), 8.07 (d, J=9.2 Hz, 1H), 7.69-7.28 (m, 23H), 7.07 (t, J=7.6 Hz, 2H), 5.67 (m, 1H), 5.22 (d, J=12 Hz, 1H), 5.86 (d, J=10.8 Hz, 1H), 4.99 (d, J=17.2 Hz, 1H), 4.85 (d, J=12 Hz, 1H), 4.70 (s, 1H), 4.15 (t, J=6.4 Hz, 1H), 3.65-3.43 (m, 2H), 3.35 (s, 2H), 3.22 (m, 1H), 2.64 (m, 1H), 2.38 (m, 1H), 1.88-1.82 (m, 2H), 1.45 (m, 1H), 1.04 (m, 1H), 0.59 (s, 9H); $^{13}$C NMR (100 MHz, CD$_3$OD) δ 169.2, 164.6, 163.4, 161.6, 161.5, 157.7, 146, 145.2, 143.9, 137, 134.8, 132.1, 132.0, 131.8, 129.7, 129.3, 128.6, 128.3, 124.1, 120.1, 118.8, 117.5, 104.9, 72.5, 64.6, 64.4, 62.3, 56.1, 54.5, 38.2, 36.1, 32.0, 27.4, 23.5, 22.7; IR (CHC13) v 3896, 3745, 3403, 3353, 3205, 2368, 2336, 2269, 1648, 1423, 1030, 772 cm$^{-1}$; [a]$_D^{23}$=+24.28 (CHCl$_3$, c=0.28); HRMS (ESI/[M-Br$^-$]$^+$): Calculated for C$_{58}$H$_{54}$C1N$_4$O$_3$ requires m/z 889.3879, found m/z 889.3881.

Example 2: Preparation of Imine Substrates

1a

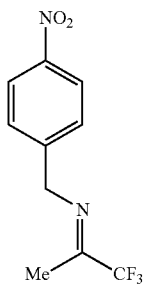

-continued

1b

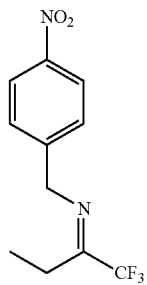

1c

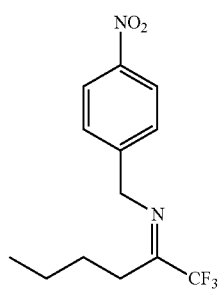

1d

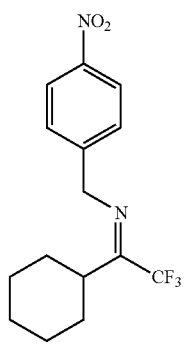

1e

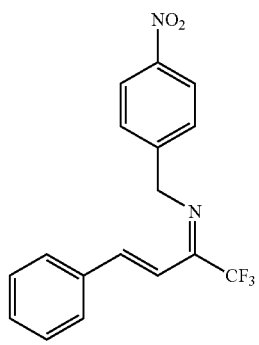

1f

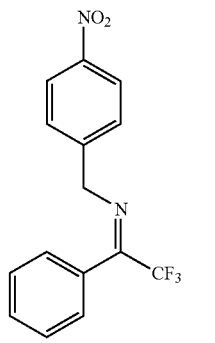

-continued

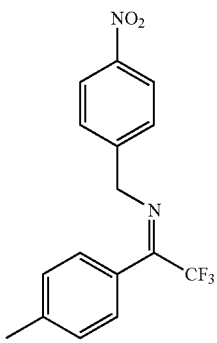
1g

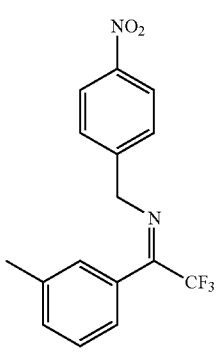
1h

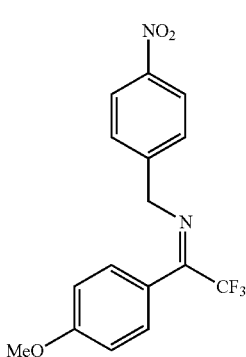
1i

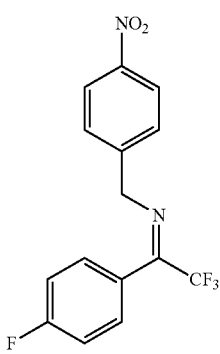
1j

Structures of Trifluoromethyl Imines

Trifluoromethyl imines (1a to 1j) were obtained according to Wu 2015 and Wu et al. *J. Am. Chem. Soc.* 2012, 134, 14334. The spectral data of the known compounds (1a to 1j) were consistent with values reported therein.

Example 3: $^1$H NMR Analysis for the Formation of QD-9c from PQD-9c in Toluene-$d_8$/CDCl$_3$

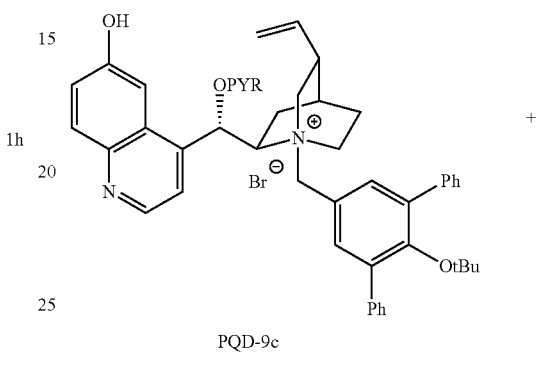
PQD-9c

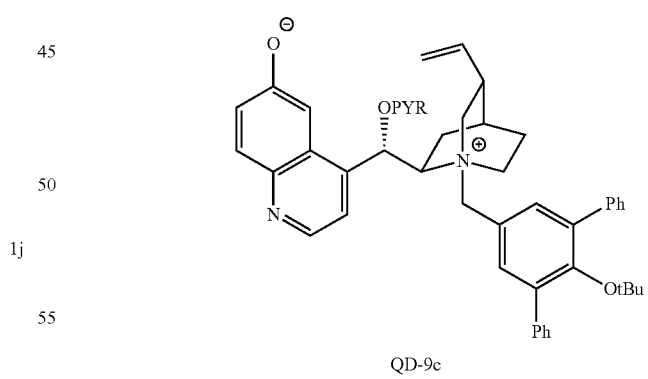
QD-9c

Figure 2:
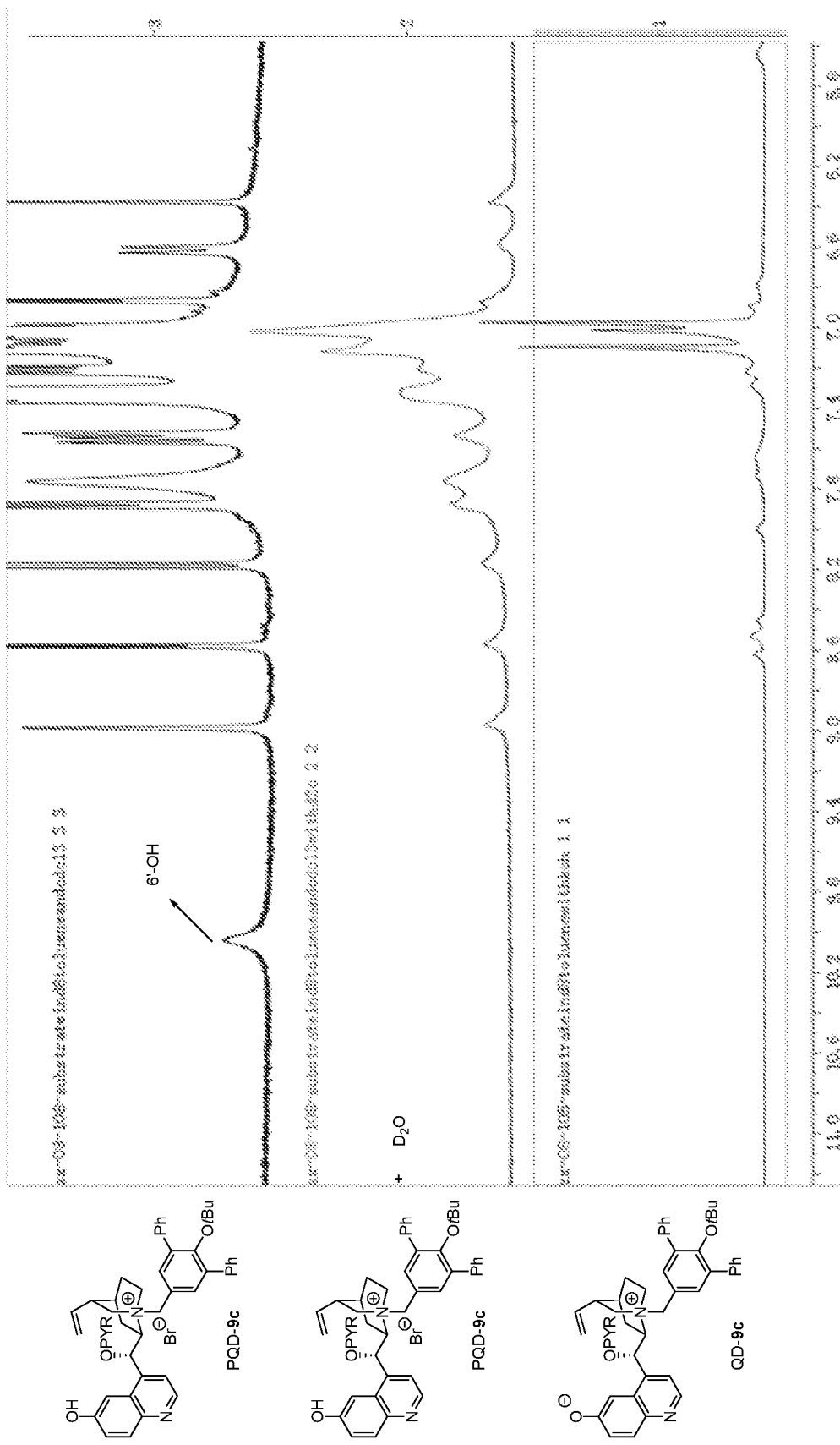
FIG. 2 depicts a partial ¾ NMR spectra of PQD-9c, PQD-9c with $D_2O$ and QD-9c in toluene-$d_8$/$CDCl_3$ at 298 K.

Betaine catalyst QD-9c was formed by treating PQD-9c (6.7 mg) at room temperature with grounded KOH solid (20.0 mg) in toluene-$d_8$/CDCl$_3$ (7/3 v/v, 0.4 mL) for 15 minutes. After standing for 15 minutes, the upper clear solution was taken by syringe and subjected directly to 1H NMR analysis. FIG. 2 shows that the 6O H proton peak in the 1H NMR spectrum of PQD-9c is not present in the spectrum of QD-9c.

Example 4: Optimization of Reaction Conditions for Asymmetric Isomerization of 1a

TABLE 4

[Reaction scheme: Ar-CH2-N=C(Me)(CF3) (1a) → Ar-CH=N-CH(Me)(CF3) (2a) + Ar-CH=N-C(Me)=CF2 (4a), with cat., Base (10 mol %), Solvent, 0.1 M, r.t., Ar = 4-NO2Ph]

| Entry | cat. | mol % of cat. | Base presented in the reaction | Solvent | t (h) | conv. (%)[b] | ee (%)[b] | 2a/4a[f] |
|---|---|---|---|---|---|---|---|---|
| 1[c] | QD-9a | 0.5 | No | Toluene/CHCl$_3$ = 7/3 | 4 | 76 | 92 | >99/1 |
| 2[c] | QD-9b | 0.5 | No | Toluene/CHCl$_3$ = 7/3 | 4 | 97 | 93 | >99/1 |
| 3[c] | QD-9c | 0.5 | No | Toluene/CHCl$_3$ = 7/3 | 4 | 98 | 95 | >99/1 |
| 4[c] | QD-9c | 0.2 | No | Toluene/CHCl$_3$ = 7/3 | 24 | 77 | 95 | >99/1 |
| 5[c] | QD-9c | 0.2 | KOH[d] | Toluene/CHCl$_3$ = 7/3 | 12 | 100 | 95 | 99/1 |
| 6[c] | QD-9c | 0.2 | solid KOH | Toluene/CHCl$_3$ = 7/3 | 12 | 100 | 95 | >99/1 |
| 7[c] | QD-9c | 0.05 | solid KOH | Toluene/CHCl$_3$ = 7/3 | 12 | 25 | 69 | 82/18 |
| 8 | — | — | solid KOH | Toluene/CHCl$_3$ = 7/3 | 12 | 3 | 0 | 27/73 |
| 9 | — | — | solid K$_2$CO$_3$ | Toluene/CHCl$_3$ = 7/3 | 12 | 0 | — | — |
| 10[e] | QD-9c | 0.2 | solid K$_2$CO$_3$ | Toluene/CHCl$_3$ = 7/3 | 12 | 100 | 95 | >99/1 |
| 11[e] | QD-9c | 0.05 | solid K$_2$CO$_3$ | Toluene/CHCl$_3$ = 7/3 | 12 | 95 | 95 | >99/1 |
| 12[f] | QD-9c | 0.05 | solid K$_2$CO$_3$ | Toluene | 6 | 100[g] | 96 | >99/1 |
| 13[f] | QD-9c | 0.02 | solid K$_2$CO$_3$ | Toluene | 24 | 100 | 96 | >99/1 |
| 14[f] | QD-9c | 0.01 | solid K$_2$CO$_3$ | Toluene | 24 | 97 | 96 | >99/1 |
| 15[h] | Q-9c | 0.05 | solid K$_2$CO$_3$ | Toluene | 24 | 100 | −93 | >99/1 |

[a]Reactions were run with 1a (0.025 mmol) in 0.25 mL solvent.
[b]Determined by HPLC analysis.
[c]Betaine catalysts QD-9 were formed from precursors PQD-9 (2.0 mg) at room temperature with grounded KOH solid (6.0 mg) in toluene/CHCl$_3$ (7/3 v/v, 0.12 mL) for 15 minutes.
[d]Aqueous KOH (0.3 μL, 50 wt %, 10 mol %) was used in the isomerization reaction.
[e]Betaine catalyst QD-9c was formed from precursors PQD-9c (2.0 mg) at room temperature with grounded K$_2$CO$_3$ solid (6.0 mg) in toluene/CHCl$_3$ (7/3 v/v, 0.12 mL) for 2 hours.
[f]Betaine catalyst QD-9c was formed from the precursor PQD-9c (2.0 mg) at room temperature with grounded K$_2$CO$_3$ solid (6.0 mg) in toluene (0.12 mL) for 2 hours.
[g]Absolute configuration was determined to be R.
[h]Betaine catalyst Q-9c was formed from the precursor PQD-9c (2.0 mg) at room temperature with grounded K$_2$CO$_3$ solid (6.0 mg) in toluene/DMF (12/1, v/v, 0.26 mL) for 2 hours.

Example 5: Isomerization of Trifluoromethyl Imines

Preparation of Deactivated Silica

The dry silica was packed in a column and washed with MeOH/Et 3N=3/1 solution [2 column volume (CV)], followed by MeOH (3 CV) and Et$_2$0 (3 CV). Then the silica was blown dry with compressed air and ready for use.

Asymmetric Isomerization of Trifluoromethyl Imine 1a with Catalyst DHQD-a

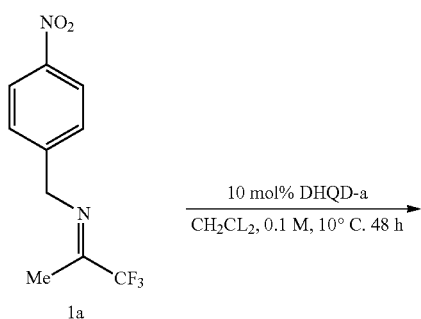

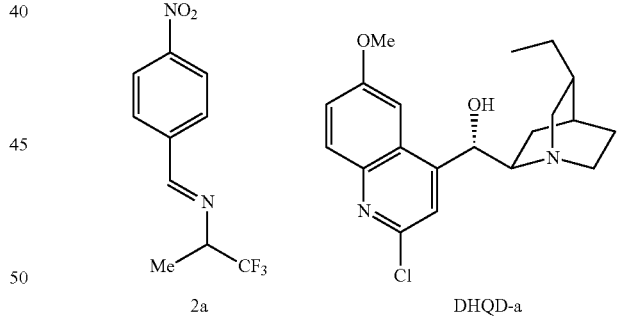

To a solution of trifluoromethyl imine 1a (0.20 mmol) in CH$_2$c 12 (1.5 mL) was added 4A molecular sieves (20 mg). The suspension was stirred at room temperature for 10 min before being moved to a 10° C. cooling bath. After the mixture was stirred at 10° C. for 20 minutes, a solution of DHQD-a (0.02 mmol) in CH$_2$c 12 (0.5 mL) was added in one portion. Then the mixture was allowed to stir at 10° C. for 48 hours. The reaction was stopped by passing the reaction mixture through a plug of deactivated silica gel to remove the catalyst. The deactivated silica gel plug was then washed with diethyl ether (2.0-4.0 mL). Trifluoromethylated amine 2a was obtained in 98% conversion and −53% ee as determined by HPLC analysis [Daicel Chiralcel AD-H, Hexanes/IPA=97/3, 1.0 ml/min, λ254 nm, 25° C., t(minor)= 12.43 min, t(major)=10.91 min].

Synthesis of Racemic Trifluoromethylated Amines:

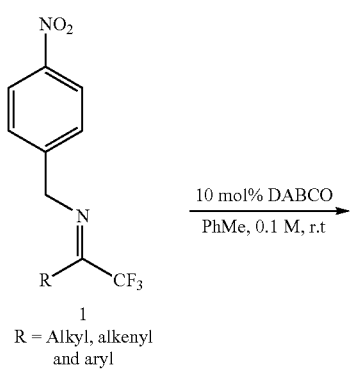

1
R = Alkyl, alkenyl and aryl

To a solution of trifluoromethyl imine 1 (0.05 mmol) in toluene (0.05 mL) was added DABCO (0.005 mmol), the mixture was stirred at room temperature until all the imine was isomerized as determined by TLC analysis. The reaction was stopped by passing the reaction mixture through a plug of deactivated silica gel to remove DABCO. The deactivated silica gel plug was then washed with diethyl ether (1.0-2.0 mL). The solvent was evaporated in vacuo to afford the pure racemic trifluoromethylated amine 2 in greater than 90% yield.

General Procedure for the Formation of Catalyst QD-9c

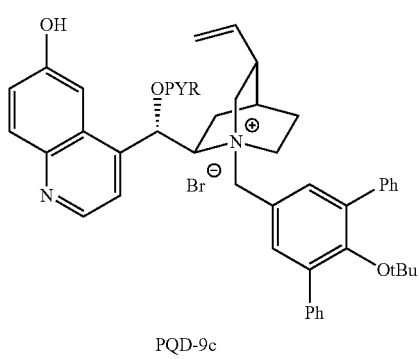

PQD-9c

K$_2$CO$_3$, Toluene, 2h, r.t.

QD-9c

To a solution of catalyst PQD-9c (3.0 mg, 0.003 1 mmol) in toluene (0.18 mL) was added grounded K$_2$CO$_3$ solid (9.0 mg, 0.019 mmol). The suspension was then stirred vigorously at room temperature for 2 hours. After standing for 10 minutes, the upper clear solution was taken and diluted by 10 times.

General Procedure for the Asymmetric Isomerization of Alkyl Trifluoromethyl Imines with Catalyst QD-9c

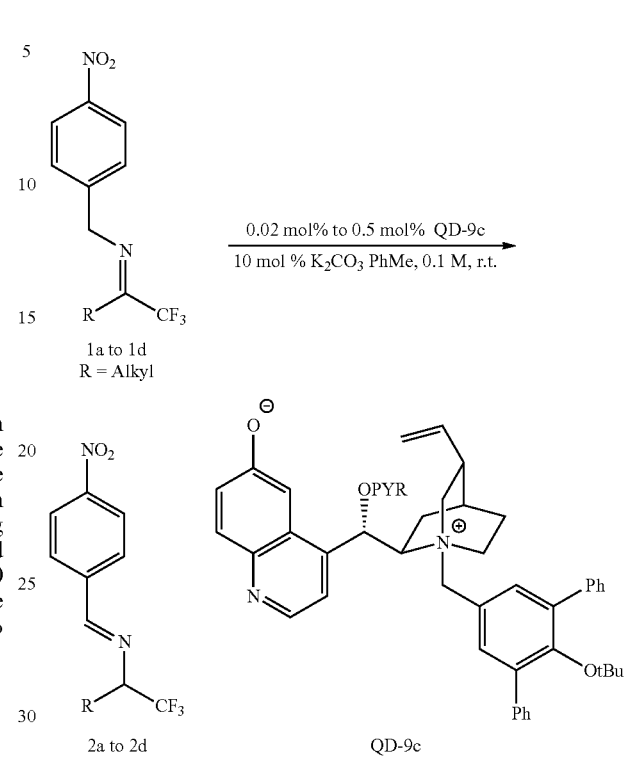

1a to 1d
R = Alkyl 2a to 2d                QD-9c

The abovementioned diluted upper clear solution of QD-9c (0.023 mL to 0.58 mL) was added into a 3.7 mL vial. To the diluted upper clear solution was added toluene (1.977 mL to 1.42 mL), grounded K$_2$CO$_3$ solid (2.8 mg, 0.02 mmol) and trifluoromethyl imine 1 (0.20 mmol) in sequence. Then the mixture was allowed to stir at room temperature for 24 hours. The reaction was stopped by passing the reaction mixture through a plug of deactivated silica gel to remove the catalyst. The deactivated silica gel plug was then washed with diethyl ether (2.0-4.0 mL). The filtrate was concentrated in vacuo to give a residue, which yielded the corresponding trifluoromethylated amines 2 without further purification.

General Procedure for the Asymmetric Isomerization of Alkenyl or Aryl Trifluoromethyl Imines with Catalyst QD-9c

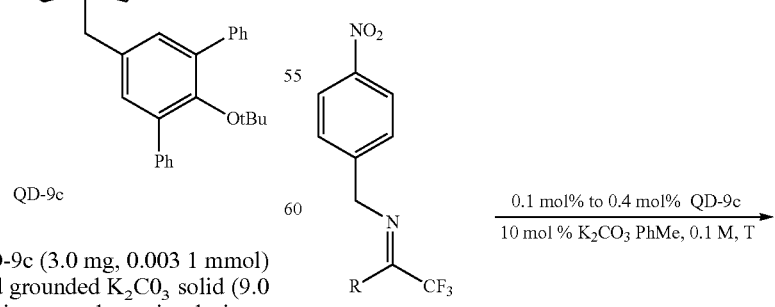

1e to 1j
R= Alkenyl or aryl

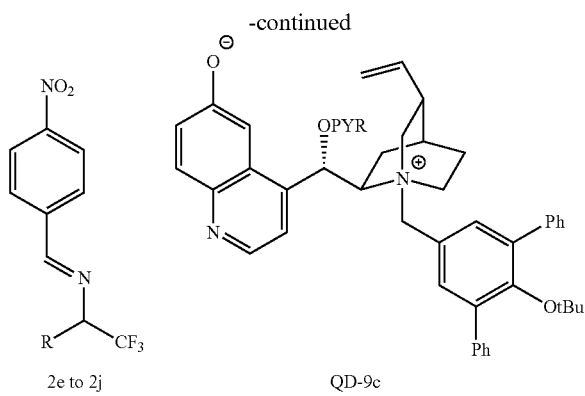

2e to 2j      QD-9c

The abovementioned diluted upper clear solution of QD-9c (0.12 mL to 0.46 mL) was added into a 3.7 mL vial. To the diluted upper clear solution was added toluene (0.68 mL to 0.34 mL) and grounded $K_2CO_3$ solid (2.8 mg, 0.02 mmol). After the mixture was stirred at the designated temperature in Table 2 for 20 minutes, the solution of imine 1 (0.2 mmol) in toluene (1.2 mL) was added in one portion (the imine solution was also stirred at the specified temperature for 20 minutes). Then the mixture was allowed to stir at the specified temperature for 24 hours. The reaction was stopped by passing the reaction mixture through a plug of deactivated silica gel to remove the catalyst. The deactivated silica gel plug was then washed with diethyl ether (2.0-4.0 mL). The filtrate was concentrated in vacuo to give a residue, which yielded the corresponding trifluoromethylated amines 2 without further purification.

General Procedure for the Formation of Catalyst Q-9c

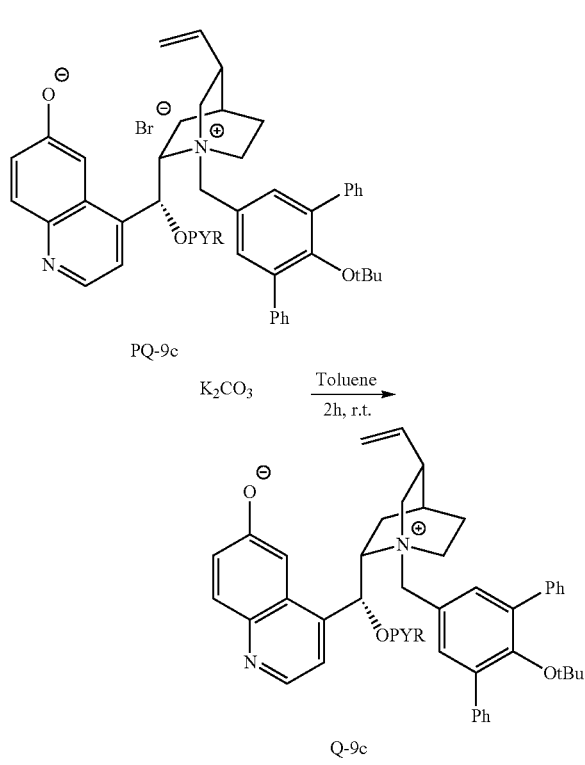

PQ-9c $K_2CO_3$    $\xrightarrow{\text{Toluene}}_{\text{2h, r.t.}}$

Q-9c

To a solution of catalyst PQ-9c (2.0 mg, 0.0021 mmol) in toluene (0.24 mL) and DMF (0.020 mL) was added grounded $K_2CO_3$ solid (6.0 mg, 0.019 mmol). The suspension was then stirred at room temperature for 2 hours. After standing for 10 minutes, the upper clear solution was taken.

General Procedure for the Asymmetric Isomerization of Alkyl Trifluoromethyl Imines with Catalyst Q-9c

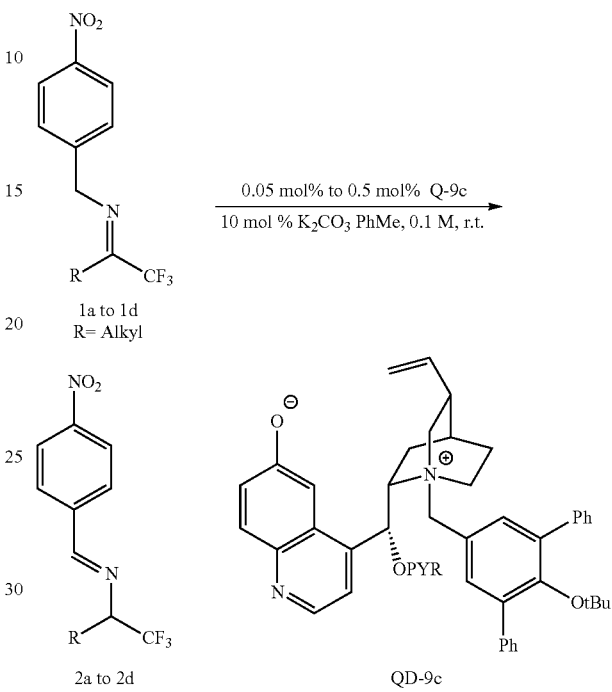

1a to 1d
R= Alkyl 2a to 2d      QD-9c

The abovementioned upper clear solution of Q-9c (0.013 mL to 0.13 mL) was added into a 3.7 mL vial. To the upper clear solution was added toluene (1.987 mL to 1.87 mL), grounded $K_2CO_3$ solid (2.8 mg, 0.02 mmol) and trifluoromethyl imine 1 (0.20 mmol) in sequence. Then the mixture was allowed to stir at room temperature for 24 hours. The reaction was stopped by passing the reaction mixture through a plug of deactivated silica gel to remove the catalyst. The deactivated silica gel plug was then washed with diethyl ether (2.0-4.0 mL). The filtrate was concentrated in vacuo to give a residue, which yielded the corresponding trifluoromethylated amines 2 without further purification (except 2d).

General Procedure for the Asymmetric Isomerization of Alkenyl or Aryl Trifluoromethyl Imines with Catalyst Q-9c 1e to 1j
R= Alkenyl or aryl

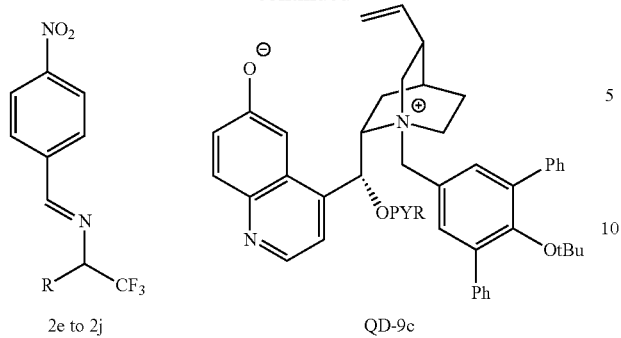

2e to 2j          QD-9c

The abovementioned upper clear solution of Q-9c (0.013 mL to 0.11 mL) was added into a 3.7 mL vial. To the upper clear solution was added toluene (0.787 mL to 0.69 mL) and grounded K$_2$CO$_3$ solid (2.8 mg, 0.02 mmol). After the mixture was stirred at the designated temperature in Table 4 for 20 minutes, the solution of imine 1 (0.2 mmol) in toluene (1.2 mL) was added in one portion (the imine solution was also stirred at the specified temperature for 20 minutes before). Then the mixture was allowed to stir at the specified temperature for 24 hours. The reaction was stopped by passing the reaction mixture through a plug of deactivated silica gel to remove the catalyst. The deactivated silica gel plug was then washed with diethyl ether (2.0-4.0 mL). The filtrate was concentrated in vacuo to give a residue, which yielded the corresponding trifluoromethylated amines 2 without further purification.

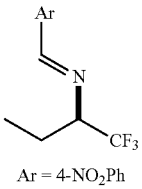

Trifluoromethylated amine 2b. This compound was obtained as a yellow liquid in 98% yield and 95% ee as determined by HPLC analysis [Daicel Chiralcel AS-H, Hexanes/IPA=90/10, 1.0 ml/min, λ254 nm, 30° C., t(major)= 8.36 min, t(minor)=17.21 min] from a reaction catalyzed by catalyst QD-9c (0.08 mol %) at room temperature for 24h. $^1$H NMR (400 MHz, CDCl$_3$) δ=8.38 (s, 1H), 8.30 (d, J=8.7 Hz, 2H), 7.99 (d, J=8.7 Hz, 2H), 3.63–3.54 (m, 1H), 2.06–1.84 (m, 2H), 0.90 (t, J=7.5 Hz, 3H); $^{13}$C NMR (100 MHz, CDCl$_3$) δ=162.8, 149.5, 140.4, 129.4, 125.1 (d, J C–F=280.2 Hz), 123.9, 73.5 (q, J C–F=27.6 Hz), 22.1 (d, J C–F=1.8 Hz), 10.0; $^{19}$F NMR (376 MHz, CDCl$_3$) δ=−75.0 (d, J=7.8 Hz). The spectral data of amine 2b were consistent with those reported in the literature (Wu 2012).

The other enantiomer was obtained in 97% yield and 91% ee as determined by HPLC analysis from a reaction catalyzed by Q-9c (0.1 mol %) at room temperature for 24h. $[α]_D^{23}$=−117.5 (CHCl$_3$, c=0.12).

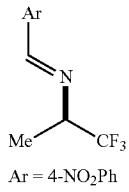

Trifluoromethylated amine 2a. This compound was obtained as a yellow solid in 96% yield and 96% ee as determined by HPLC analysis [Daicel Chiralcel AD-H, Hexanes/IPA=97/3, 1.0 ml/min, λ254 nm, 25° C., t(major)= 12.43 min, t(minor)=10.9 min] from a reaction catalyzed by catalyst QD-9c (0.02 mol %) at room temperature for 24h. $^1$H NMR (400 MHz, CDCl$_3$) δ=8.43 (s, 1H), 8.29 (d, J=8.6 Hz, 2H), 7.97 (d, J=8.6 Hz, 2H), 3.98–3.87 (m, 1H), 1.47 (d, J=6.7 Hz, 3H); $^{13}$C NMR (100 MHz, CDCl$_3$) δ=162.2, 149.5, 140.6, 129.3, 125.3 (d, J C–F=278.2 Hz), 123.9, 66.6 (q, J C–F=29 Hz), 15.6 (d, J C–F=2.0 Hz); $^{19}$F NMR (376 MHz, CDCl$_3$) δ=−76.7 (d, J=7.2 Hz); $[α]_D^{23}$=+91.8 (CHCl$_3$, c=0.40). The spectral data of amine 2a were consistent with those reported in the literature (Wu 2012).

The absolute configuration of (+)—2a was determined to be R by comparing the specific optical rotation with the literature value. $[α]_D^{23}$=+91.8 (CHCl$_3$, c=0.40) for 96% ee [lit. $[α]_D^{23}$=+73.7 (CHCl$_3$, c=0.19) for 90% ee].

The other enantiomer was obtained in 96% yield and 93% ee as determined by HPLC analysis from a reaction catalyzed by Q-9c (0.05 mol %) at room temperature for 24h. $[α]_D^{23}$=−85.1 (CHCl$_3$, c=0.43).

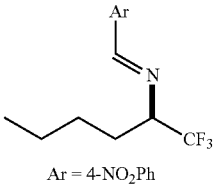

Trifluoromethylated amine 2c. This compound obtained as a yellow solid in 97% yield and 96% ee as determined by HPLC analysis [Daicel Chiralcel OJ-H, Hexanes/IPA=80/20, 1.0 ml/min, λ254 nm, 25° C., t(major)=7.38 min, t(minor)=6.98 min] from a reaction catalyzed by catalyst QD-9c (0.1 mol %) at room temperature for 24h. $^1$H NMR (400 MHz, CDCl$_3$) δ=8.37 (s, 1H), 8.30 (d, J=8.8 Hz, 2H), 7.98 (d, J=8.8 Hz, 2H), 3.71–3.62 (m, 1H), 1.97–1.83 (m, 2H), 1.43–1.12 (m, 4H), 0.90 (d, J=7.2 Hz, 3H); $^{13}$C NMR (100 MHz, CDCl$_3$) δ=162.7, 149.5, 140.4, 129.4, 125.2 (d, J C–F=279.0 Hz), 123.9, 72.1 (q, J C–F=27.5 Hz), 28.4 (d, J C–F=1.6 Hz), 27.5, 22.2, 13.8; $^{19}$F NMR (376 MHz, CDCl$_3$) δ=−75.1 (d, I=6.8 Hz). The spectral data of amine 2c were consistent with those reported in the literature (Wu 2012).

The other enantiomer was obtained in 96% yield and 90% ee as determined by HPLC analysis from a reaction catalyzed by Q-9c (0.2 mol %) at room temperature for 24h. $[α]_D^{23}$=−156.1 (CHCl$_3$, c=0.57).

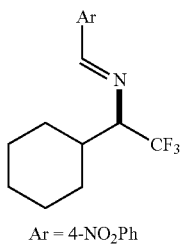

Ar = 4-NO₂Ph

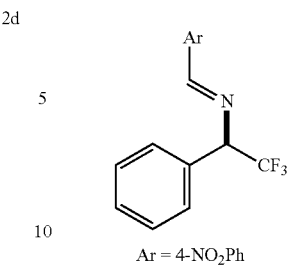

Ar = 4-NO₂Ph

Trifluoromethylated amine 2d. This compound was obtained as a yellow liquid in 97% yield and 94% ee as determined by HPLC analysis [Daicel Chiralcel AS-H, Hexanes/IPA=90/10, 1.0 ml/min, λ254 nm, 25° C., t(major)= 5.89 min, t(minor)=25.09 min] from a reaction catalyzed by catalyst QD-9c (0.5 mol %) at room temperature for 24h. $^{1}$H NMR (400 MHz, CDCl$_3$) δ=8.32 (s, 1H), 8.30 (d, J=8.8 Hz, 2H), 7.98 (d, J=8.8 Hz, 2H), 3.51-3.44 (m, 1H), 2.07-1.98 (m, 1H), 1.85-1.65 (m, 5H), 1.38-1.20 (m, 2H), 1.16-1.03 (m, 3H); $^{13}$C NMR (100 MHz, CDCl$_3$) δ=162.7, 149.5, 140.5, 129.4, 125.2 (d, J C–F=281.7 Hz), 123.9, 76.9 (q, J C–F=26.1 Hz), 38.2, 30.2, 28.4, 26.1, 25.9; $^{19}$F NMR (376 MHz, CDCl$_3$) δ=−70.6 (d, J=8.1 Hz). The spectral data of amine 2d were consistent with those reported in the literature (Wu 2012).

The other enantiomer was obtained by flash chromatography (Hexanes/CH$_2$Cl$_2$=10/1, deactivated silica gel) in 74% yield and 86% ee as determined by HPLC analysis from a reaction catalyzed by Q-9c (0.5 mol %) at room temperature for 24h. $[α]_D^{23}$=−174.3 (CHCl$_3$, c=0.46).

Trifluoromethylated amine 2f. This compound was obtained as a yellow liquid in 96% yield and 90% ee as determined by HPLC analysis [Daicel Chiralcel AD, Hexanes/IPA=80/20, 1.0 ml/min, λ254 nm, 25° C., t(major)= 8.38 min, t(minor)=12.11 min] from a reaction catalyzed by catalyst QD-9c (0.1 mol %) at 0° C. for 24h. $^{1}$H NMR (400 MHz, CDCl$_3$) δ=8.47 (s, 1H), 8.29 (d, J=8.4 Hz, 2H), 8.01 (d, J=8.4 Hz, 2H), 7.56-7.54 (m, 2H), 7.44-7.41 (m, 3H), 4.87 (q, J=7.5 Hz, 1H); $^{13}$C NMR (100 MHz, CDCl$_3$) δ=163.6, 149.7, 140.5, 134.2, 129.5, 129.3, 128.8, 128.7, 124.4 (d, J C–F=280.9 Hz), 123.9, 125.1 (q, J C–=29 Hz); $^{19}$F NMR (376 MHz, CDCl$_3$) δ=−74.1 (d, J=7.1 Hz); $[α]_D^{23}$=+233.0 (CHCl$_3$, c=0.40). The spectral data of amine 2f were consistent with those reported in the literature (Wu 2012).

The absolute configuration of (+)-2f was determined to be R by comparing the specific optical rotation with literature value (Wu 2012). $[α]_D^{23}$=+233.0 (CHCl$_3$, c=0.40) for 90% ee [lit. $[α]_D^{23}$=+205.3 (CHCl$_3$, c=0.53)]. The other enantiomer was obtained in 96% yield and 81% ee as determined by HPLC analysis from a reaction catalyzed by Q-9c (0.1 mol %) at 0° C. for 24h. $[α]_D^{23}$=−187.3 (CHCl$_3$, c=0.52).

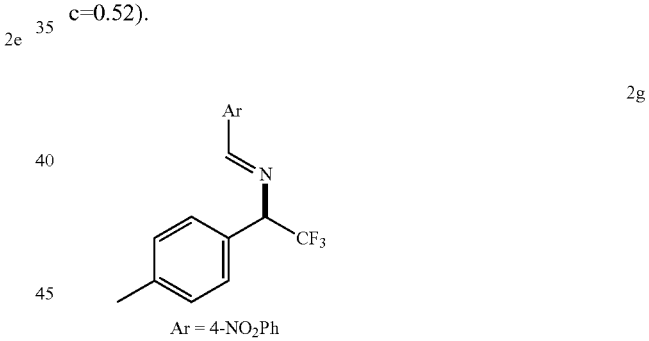

Ar = 4-NO₂Ph (left structure labeled 2e); Ar = 4-NO₂Ph (right structure labeled 2g)

Trifluoromethylated amine 2e. This compound was obtained as a yellow liquid in 97% yield and 95% ee as determined by HPLC analysis [Daicel Chiralcel AS-H, Hexanes/IPA=80/20, 1.0 ml/min, λ254 nm, 25° C., t(major)= 6.01 min, t(minor)=8.47 min] from a reaction catalyzed by catalyst QD-9c (0.4 mol %) at 0° C. for 24h. $^{1}$H NMR (400 MHz, CDCl$_3$) δ=8.49 (s, 1H), 8.29 (d, J=8.8 Hz, 2H), 8.00 (d, J=8.8 Hz, 2H), 7.44-7.42 (m, 2H), 7.37-7.28 (m, 3H), 6.75 (d, J=16, 1H), 6.34 (dd, J=16, 7.4 Hz, 1H), 4.57-4.49 (m, 1H); $^{13}$C NMR (100 MHz, CDCl$_3$) δ=163.4, 149.7, 140.5, 136.8, 135.4, 129.5, 128.7, 126.8, 124.5 (q, J C–F=280.3 Hz), 123.9, 120.5 (d, J C–F=1.9 Hz), 73.2 (q, J C–F=29.1 Hz); $^{19}$F NMR (376 MHz, CDCl$_3$) δ=−74.9 (d, J=7.1 Hz); IR (CHCl$_3$) v 2360, 2335, 1648, 1604, 1526, 1348, 1261, 1172, 1127, 757 cm$^{-1}$; $[α]_D^{23}$=+103.0 (CHCl$_3$, c=0.43); HIRMS (ESI/[M+H]$^+$): Calculated for C$_{17}$H$_{14}$F$_3$N$_2$O$_2$ requires m/z 335.1007, found m/z 335.1006.

The other enantiomer was obtained in 96% yield and 85% ee as determined by HPLC analysis from a reaction catalyzed by Q-9c (0.4 mol %) at 0° C. for 24h. $[α]_D^{23}$=−78.9 (CHCl$_3$, c=0.61).

Trifluoromethylated amine 2g. This compound was obtained as a yellow liquid in 99% yield and 93% ee as determined by HPLC analysis [Daicel Chiralcel OJ-H, Hexanes/IPA=70/30, 1.0 ml/min, λ254 nm, 25° C., t(major)=20.82 min, t(minor)=17.15 min] from a reaction catalyzed by catalyst QD-9c (0.1 mol %) at 0° C. for 24h. $^{1}$H NMR (400 MHz, CDCl$_3$) δ=8.45 (s, 1H), 8.29 (d, J=8.8 Hz, 2H), 8.00 (d, J=8.8 Hz, 2H), 7.42 (d, J=7.9 Hz, 2H), 7.26 (s, 1H), 7.22 (d, J=7.9 Hz, 2H), 4.84 (q, J=7.5 Hz, 1H), 2.37 (s, 3H); $^{13}$C NMR (100 MHz, CDCl$_3$) δ=163.3, 149.6, 140.6, 139.3, 131.3, 129.5, 128.6, 124.4 (q, J C–F=280.8 Hz), 123.9, 74.8 (q, J C–F=29 Hz), 21.2; $^{19}$F NMR (376 MHz, CDCl$_3$) δ=−74.3 (d, J=7.1 Hz). The spectral data of amine 2g were consistent with those reported in the literature (Wu 2012).

The other enantiomer was obtained in 97% yield and 85% ee as determined by HPLC analysis from a reaction catalyzed by Q-9c (0.1 mol %) at 0° C. for 24h. $[α]_D^{23}$=−183.8 (CHCl$_3$, c=0.58).

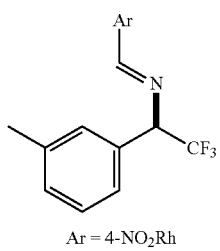

Ar = 4-NO₂Rh

Trifluoromethylated amine 2h. This compound was obtained as a yellow liquid in 98% yield and 93% ee as determined by HPLC analysis [Daicel Chiralcel OJ-H, Hexanes/IPA=80/20, 1.0 ml/min, λ254 nm, 25° C., t(major)=27.85 min, t(minor)=18.76 min] from a reaction catalyzed by catalyst QD-9c (0.1 mol %) at 0° C. for 24h. $^1$H NMR (400 MHz, CDCl₃) δ=8.46 (s, 1H), 8.29 (d, J=8.7 Hz, 2H), 8.01 (d, J=8.7 Hz, 2H), 7.35-7.20 (m, 4H), 4.83 (q, J=7.5 Hz, 1H), 2.39 (s, 3H); $^{13}$C NMR (100 MHz, CDCl₃) δ=163.4, 149.6, 140.5, 138.6, 134.1, 130, 129.5, 129.3, 128.7, 128.2, 125.8, 124.4 (q, J C-F=280.5 Hz), 123.9, 75.1 (q, J C-F=29 Hz), 21.4; $^{19}$F NMR (376 MHz, CDCl₃) δ=-74.1 (d, J=6.9 Hz). The spectral data of amine 2h were consistent with those reported in the literature (Wu 2012).

The other enantiomer was obtained in 98% yield and 84% ee as determined by HPLC analysis from a reaction catalyzed by Q-9c (0.1 mol %) at 0° C. for 24h. $[\alpha]_D^{23}$=-194.7 (CHCl₃, c=0.57).

2i

Trifluoromethylated amine 2i. This compound obtained as a yellow liquid in 99% yield and 93% ee as determined by HPLC analysis [Daicel Chiralcel AD-H, Hexanes/IPA=80/20, 1.0 ml/min, λ254 nm, 25° C., t(major)=12.39 min, t(minor)=14.86 min] from a reaction catalyzed by catalyst QD-9c (0.1 mol %) at 0° C. for 24h. $^1$H NMR (400 MHz, CDCl₃) δ=8.45 (s, 1H), 8.28 (d, J=8.8 Hz, 2H), 8.00 (d, J=8.8 Hz, 2H), 7.46 (d, J=8.6 Hz, 2H), 6.94 (d, J=8.6 Hz, 2H), 4.83 (q, J=7.5 Hz, 1H), 3.82 (s, 3H); $^{13}$C NMR (100 MHz, CDCl₃) δ=163.3, 160.2, 149.6, 140.6, 129.9, 129.5, 126.2, 124.5 (q, J C-F=281.9 Hz), 123.9, 114.2, 74.5 (q, J C-F=28.9 Hz), 55.3; $^{19}$F NMR (376 MHz, CDCl₃) δ=-74.5 (d, J=6.9 Hz). The spectral data of amine 2i were consistent with those reported in the literature (Wu 2012).

The other enantiomer was obtained in 96% yield and 84% ee as determined by HPLC analysis from a reaction catalyzed by Q-9c (0.1 mol %) at 0° C. for 24h. $[\alpha]_D^{23}$=-182.8 (CHC₃, c=0.60).

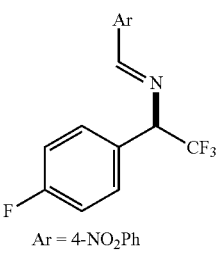

Ar = 4-NO₂Ph

Trifluoromethylated amine 2j. This compound was obtained as a yellow liquid in 97% yield and 90% ee as determined by HPLC analysis [Daicel Chiralcel OJ-H, Hexanes/IPA=70/30, 1.0 ml/min, t(major)=19.91 min, t(minor)=13.01 min] from a reaction catalyzed by catalyst QD-9c (0.2 mol %) at -20° C. for 24 h. 1H NMR (400 MHz, CDCl₃) δ=8.48 (s, 1H), 8.30 (d, J=8.8 Hz, 2H), 8.02 (d, J=8.8 Hz, 2H), 7.54 (dd, J=5.6, 8.3 Hz, 2H), 7.1 1 (t, J=8.7 Hz, 2H), 4.86 (q, J=7.3, 1H); $^{13}$CNMR (100 MHz, CDCl₃) δ=164.4, 163.8, 161.9, 149.7, 140.4, 130.5, 130.4, 130, 124.2 (q, 7C—F=280.5 Hz), 123.9, 115.9, 115.7, 74.4 (q, 7C—F=29.0 Hz); $^{19}$F NMR (376 MHz, CDCl₃) δ=-74.5 (d, 7=6.9 Hz). The spectral data of amine 2j were consistent with those reported in the literature (Wu 2012).

The other enantiomer was obtained in 95% yield and 79% ee as determined by HPLC analysis from a reaction catalyzed by Q-9c (0.05 mol %) at -20° C. for 24 h. $[a]o^{23}$=-173.1 (CHCI₃, c=0.64).

The disclosures of each and every patent, patent application, and publication cited herein are hereby incorporated herein by reference in their entirety.

While the disclosure has referenced specific embodiments, it is apparent that other embodiments and variations may be devised by others skilled in the art without departing from the true spirit and scope of the invention. The appended claims are intended to be construed to include all such embodiments and equivalent variations.

What is claimed:

1. A compound, or a salt, tautomer, enantiomer or diastereoisomer thereof, of formula (I):

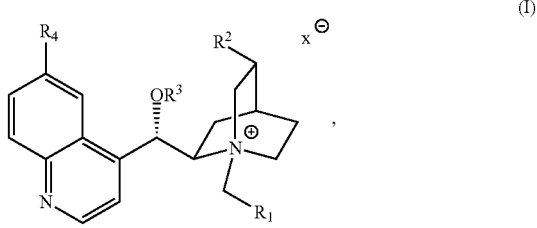

wherein:

R¹ is

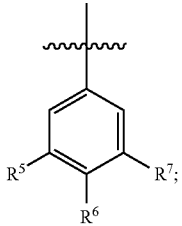

R⁵ and R⁷ are independently aryl;
R⁶ is alkoxy or alkylsiloxy;
R² is alkenyl;
R³ is optionally substituted heteroaryl, where each optional substituent is independently selected from aryl and halo;
X⁻ is a negative counterion; and
R⁴ is —OH.

2. The compound of claim 1, wherein R₅ and R₇ are each phenyl.

3. The compound of claim 1, wherein R₆ is selected from methoxy, t-butoxy and t-butyldimethylsiloxy.

4. The compound of claim 1, wherein R₂ is —CH=CH₂.

5. The compound of claim 1, wherein R₃ is 4-chloro-2,5-diphenylpyrimidinyl or pyrimidinyl substituted with one or more groups selected from aryl and halo.

6. The compound of claim 1, which is selected from:

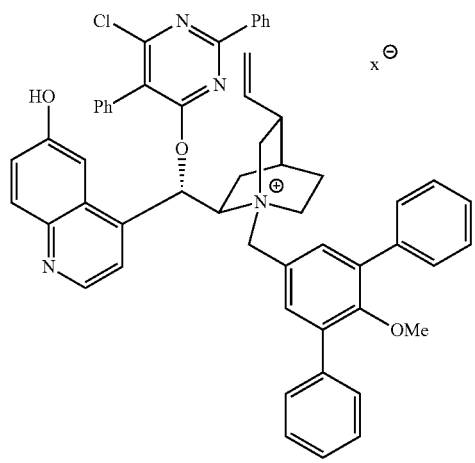 [SMILES: C=CC1C[N+]2(Cc3cc(-c4ccccc4)c(OC)c(-c4ccccc4)c3)CCC1CC2[C@@H](Oc1nc(-c2ccccc2)nc(Cl)c1-c1ccccc1)c1ccnc2ccc(O)cc12]

(1S,2R,4S,5R)-2-((S)-((6-chloro-2,5-diphenylpyrimidin-4-yl)oxy)(6-hydroxyquinolin-4-yl)methyl)-1-((2'-methoxy-[1,1':3',1''-terphenyl]-5'-yl)methyl)-5-vinylquinuclidin-1-ium (PQD-9);

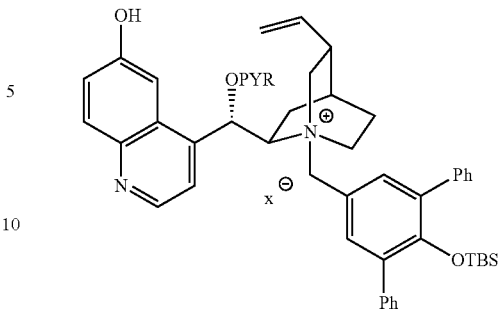

(1S,2R,4S,5R)-2-((S)-((6-chloro-2,5-diphenylpyrimidin-4-yl)oxy)(6-hydroxyquinolin-4-yl)methyl)-1-((2'-(tert-butyldimethylsilyl)oxy)-[1,1':3',1''-terphenyl]-5'-yl)methyl)-5-vinylquinuclidin-1-ium (PQD-9b); and

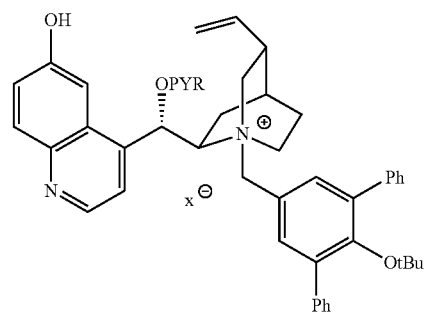

(1S,2R,4S,5R)-2-((S)-((6-chloro-2,5-diphenylpyrimidin-4-yl)oxy)(6-hydroxyquinolin-4-yl)methyl)-1-((2' (tert-butoxy) [1,1':3',1''-terphenyl]-5'-yl)methyl)-5-vinylquinuclidin-1-ium (PQD-9c).

7. A method of promoting imine isomerization that comprises contacting the imine with at least one compound of claim 1, wherein the imine comprises formula (II):

wherein:
Rᵃ is selected from optionally substituted alkyl, optionally substituted aryl, optionally substituted cycloalkyl, and optionally substituted alkenyl, where each optional substituent is independently selected from alkyl, alkoxy, and halo;
Rᵇ is trifluoromethyl; and
Rᶜ is aryl optionally substituted with nitro;

to afford a compound a compound of formula (III)

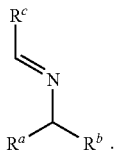

8. The method of claim 7, wherein $R^a$ is alkyl selected from methyl, ethyl and n-butyl.

9. The method of claim 7, wherein $R^a$ is cyclohexyl.

10. The method of claim 7, wherein $R^a$ is phenyl, optionally substituted with methyl, methoxy or fluoro.

11. The method of claim 7, wherein $R^c$ is phenyl substituted with nitro.

12. The method of claim 7, wherein the imine and the at least one compound are contacted in a non-aqueous system in the presence of a base.

13. The method of claim 12, wherein the base is NaOH or KOH.

14. The method of claim 12, wherein the base is $Na_2CO_3$ or $K_2CO_3$.

15. The method of claim 7, wherein the amount of the at least one compound ranges from about 0.01 mol % to about 0.1 mol % with respect to the imine.

16. The method of claim 7, wherein the at least one compound is selected from:

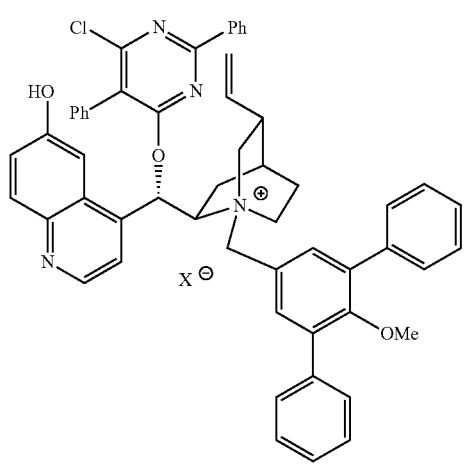

(1S,2R,4S,5R)-2-((S)-((6-chloro-2,5-diphenylpyrimidin-4-yl)oxy)(6-hydroxyquinolin-4-yl)methyl)-1-((2'-methoxy-[1,1':3',1''-terphenyl]-5'-yl)methyl)-5-vinylquinuclidin-1-ium (PQD-9);

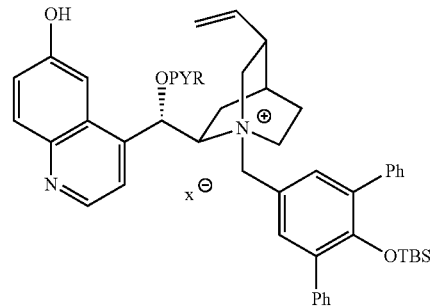

(1S,2R,4S,5R)-2-((S)-((6-chloro-2,5-diphenylpyrimidin-4-yl)oxy)(6-hydroxyquinolin-4-yl)methyl)-1-((2'-(tert-butyldimethylsilyl)oxy)-[1,1':3',1''-terphenyl]-5'-yl)methyl)-5-vinylquinuclidin-1-ium (PQD-9b); and

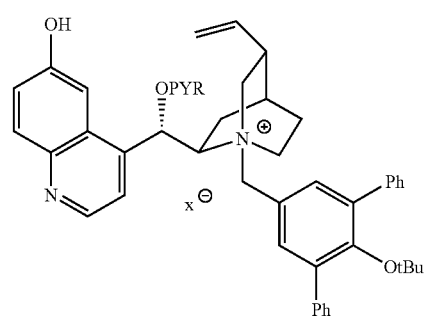

(1S,2R,4S,5R)-2-((S)-((6-chloro-2,5-diphenylpyrimidin-4-yl)oxy)(6-hydroxyquinolin-4-yl)methyl)-1-((2' (tert-butoxy)[1,1': 3',1''-terphenyl]-5'-yl)methyl)-5-vinylquinuclidin-1-ium (PQD-9c).

17. A compound, or a salt, tautomer, enantiomer or diastereoisomer thereof, of formula (QD-8):

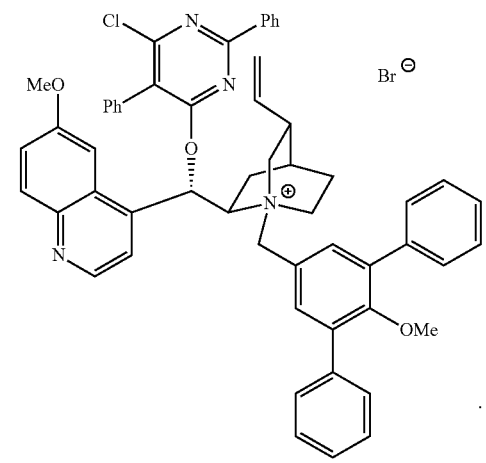 [SMILES: C=CC1C[N+]2(Cc3cc(-c4ccccc4)c(OC)c(-c4ccccc4)c3)CCC1CC2[C@@H](Oc1nc(-c2ccccc2)nc(Cl)c1-c1ccccc1)c1ccnc2ccc(OC)cc12 ; [Br-]]

18. The compound of claim 1, wherein $X^-$ is $Br^-$.

19. The compound of claim 1, wherein $X^-$ is $Cl^-$ or $I^-$.

20. A method of promoting imine isomerization that comprises contacting the imine with at least one compound of claim 17, wherein the imine comprises formula (II):

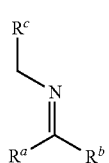

(II)

wherein:
R$^a$ is selected from optionally substituted alkyl, optionally substituted aryl, optionally substituted cycloalkyl, and optionally substituted alkenyl, where each optional substituent is independently selected from alkyl, alkoxy, and halo;
R$^b$ is trifluoromethyl; and
R$^c$ is aryl optionally substituted with nitro;
to afford a compound a compound of formula (III)

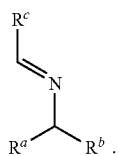

(III)

* * * * *